(12) United States Patent
Laeng et al.

(10) Patent No.: US 7,132,286 B2
(45) Date of Patent: Nov. 7, 2006

(54) METHOD FOR NEURAL STEM CELL DIFFERENTIATION USING VALPROATE

(75) Inventors: Pascal Laeng, Washington, DC (US); Barbara Mallon, Gaithersburg, MD (US); Lee Pitts, Falls Church, VA (US)

(73) Assignee: Psychiatric Genomics, Inc., Gaithersburg, MD (US)

( * ) Notice: Subject to any disclaimer, the term of this patent is extended or adjusted under 35 U.S.C. 154(b) by 264 days.

(21) Appl. No.: 10/175,168

(22) Filed: Jun. 18, 2002

(65) Prior Publication Data
US 2003/0013192 A1 Jan. 16, 2003

Related U.S. Application Data

(60) Provisional application No. 60/299,066, filed on Jun. 18, 2001.

(51) Int. Cl.
C12N 5/02 (2006.01)
C12Q 1/02 (2006.01)
C12N 5/06 (2006.01)
C12N 5/08 (2006.01)

(52) U.S. Cl. ................ 435/377; 435/29; 435/352; 435/363

(58) Field of Classification Search ............... 435/377; 514/724; 424/93.1
See application file for complete search history.

(56) References Cited

U.S. PATENT DOCUMENTS

| | | | |
|---|---|---|---|
| 5,672,746 A | 9/1997 | Nau et al. | 562/598 |
| 5,753,506 A | 5/1998 | Johe et al. | 435/377 |
| 5,766,948 A | 6/1998 | Gage et al. | 435/368 |
| 5,851,832 A | 12/1998 | Weiss et al. | 435/368 |
| 6,103,530 A | 8/2000 | Carpenter et al. | 435/405 |
| 6,149,902 A | 11/2000 | Artavanis-Tsakonas et al. | 424/93.1 |

OTHER PUBLICATIONS

Barker et al. Neural transplantation therapies for Parkinson's and Huntington's diseases. Drug Discov Today. Jun. 1, 2001;6(11):575-582.*
Freeman et al. Bilateral fetal nigral transplantation into the postcommissural putamen in Parkinson's disease. Ann Neurol. Sep. 1995;38(3):379-88.*
Isacson O. The production and use of cells as therapeutic agents in neurodegenerative diseases. Lancet Neurol. Jul. 2003;2(7):417-24.*
Kordower et al. Neuropathological evidence of graft survival and striatal reinnervation after the transplantation of fetal mesencephalic tissue in a patient with Parkinson's disease. N Engl J Med. Apr. 27, 1995;332(17):1118-24.*
Lindvall et al. Stem cell therapy for human neurodegenerative disorders-how to make it work. Nat Med. Jul. 2004;10 Suppl:S42-50.*
Neophytides et al. Sodium valproate in the treatment of cerebellar disorders. Can J Neurol Sci. Nov. 1979;6(4):455-7.*
Nutt et al. Treatment of Parkinson's disease with sodium valproate: clinical, pharmacological, and biochemical observations. Can J Neurol Sci. Aug. 1979;6(3):337-43.*
Pearce et. al Valproate sodium in Huntington chorea. Arch Neurol. May 1977;34(5):308-9.*
Price et al. Sodium valproate in the treatment of levodopa-induced dyskinesia. J Neurol Neurosurg Psychiatry. Aug. 1978;41(8):702-6.*
Symington et al. Sodium valproate in Huntington's disease. Am J Psychiatry. Mar. 1978;135(3):352-4.*
Weissman IL. Translating stem and progenitor cell biology to the clinic: barriers and opportunities. Science. Feb. 25, 2000;287(5457):1442-6.*
Widner et al. Bilateral fetal mesencephalic grafting in two patients with parkinsonism induced by 1-methyl-4-phenyl-1,2,3,6-tetrahydropyridine (MPTP) N Engl J Med. Nov. 26, 1992;327(22):1556-63.*
Tariot et al. Safety and tolerability of divalproex sodium in the treatment of signs and symptoms of mania in elderly patients with dementia: Results of a double-blind, placebo-controlled trial. Current Therapeutics Research (2001), 62(1), 51-67.*
Mattson MP. Stem cells as therapeutics for neurodegenerative disorders? Exp. Rev. Neurotherap. (2001), 1(2), 267-273.*
Herrmann N. Pharmacotherapy for Alzheimer's disease and other dementias. Curr. Opin. Psychiatry (2002), 15:403-409.*
Mosby's GenRx (1998) Drug Information "Valproate Sodium" and "Valproic Acid", Mosby, Baltimore, pp. II-2164-II-2171.*
Cinatl et al. Antitumor activity of sodium valproate in cultures of human neuroblastoma cells. Anticancer Drugs. Sep. 1996;7(7):766-73.*
Regan et al. In vitro screening for anitconvulsant-induced teratogenesis in neural primary cultures and cell lines. Int. J. Neurosci. 1990; 8(2):143-150.*
Loo et al. Differentiation of serum-free mouse embryo cells into astrocytes is accompanied by induction of glutamine synthetase activity. J Neurosci Res. Oct. 1, 1995;42(2):184-91.*
Lukaszewicz et al. Contrasting effects of basic fibroblast growth factor and neurotrophin 3 on cell cycle kinetics of mouse cortical stem cells. J Neurosci. Aug. 1, 2002;22(15):6610-22.*
Vescovi et al. Isolation and cloning of multipotential stem cells from the embryonic human CNS and establishment of transplantable human neural stem cell lines by epigenetic stimulation. Exp Neurol. Mar. 1999;156(1):71-83.*
Shetty and Turner, J Neurobiol. 1998;35:395-425.
Skladchikova et al., Neurotoxicol. 1998;19:357-70.
Cinatl et al., Anticancer Drugs 1996;7:766-73.
Slesinger and Singer, Epilepsia 1987; 28:214-21.
Knupfer et al., Anticancer Res 1998; 21:347-51.
Yuan et al, J Biol Chem 2001; 276:31674-83.

(Continued)

*Primary Examiner*—Daniel M. Sullivan
(74) *Attorney, Agent, or Firm*—Darby & Darby

(57) ABSTRACT

The present invention relates to a method for differentiating a neural stem cell into a neuronal cell such as a neuroblast or neuron in vitro or in vivo. Particularly, the invention provides for a method for neural stem cell differentiation by contacting the neural stem cell with a valproate compound or analog thereof.

21 Claims, 10 Drawing Sheets
(2 of 10 Drawing Sheet(s) Filed in Color)

OTHER PUBLICATIONS

Gottlicher et al., Embo J 1998; 20:6969-78.

Manji et al., Biol Psychiatry 2000;48:740-54.

Regan et al., Brain Res 1985; 347:394-98.

Werling et all, Mol Pharmacol 2001; 59:1269-76.

Ourednik et al., "Neural Stem Cells—A Versatile Tool for Cell Replacement and Gene Therapy in the Central Nervous System," *Clin Genet.*, Oct. 1999, vol. 56, No. 4, pp. 267-278.

Abe, :Therapeutic Potential of Neurotrophic Factors and Neural Stem Cells Against Ischemic Brain Injury, *J. Cereb. Blood Flow Metab.*, Oct. 2000, vol. 20, No. 10, pp. 1393-1408.

Sanchez-Ramos, et al., "Adult Bone Marrow Stromal Cells Differentiate Into Neural Cells *In Vitro*," *Exp. Neurol.*, Aug. 2000, vol. 164, No. 2, pp. 247-256.

Himelhoch, et al., "Extreme Mood Lability Associated With Systemic Lupus Erythematosus and Stroke Successfully Treated With Valproic Acid," *J Clin Psychopharmacol*, Dec. 1996, vol. 16, No. 6, pp. 469-470.

Wallce, "Myoclonus and Epilepsy in Childhood: A Review of Treatment With Valproate, Ethosuximide, Lamotrigine and Zonisamide," *Epilepsy Res.*, Jan. 1998, vol. 29, No. 2, pp. 147-154.

Kahn et al., "Effect of Sodium Valproate in Three Patients With Organic Brain Syndromes," *Am. J. Psychiatry*, Aug. 1988, vol. 145, No. 8, pp. 1010-1011.

* cited by examiner

METHOD FOR NEURAL STEM CELL DIFFERENTIATION USING VALPROATE

This application claims priority from U.S. Provisional Application Ser. No. 60/299,066, filed Jun. 18, 2001, hereby incorporated herein by reference.

FIELD OF THE INVENTION

The present invention relates to methods for cell cultivation and differentiation. In particular, the invention relates to methods for cultivating and differentiating neural stem cells using valproate.

BACKGROUND

Neural stem cells have been isolated from various regions of both rodent and human nervous systems and expanded in vitro as free floating aggregates (U.S. Pat. No. 5,851,832 to Weiss et al.) or as a monolayer attached to a substratum-coated dish (U.S. Pat. No. 5,753,506 to Johe). Neural stem cells are capable of extended self-renewal and have the ability, under appropriate conditions, to generate one or more subtypes of neurons and glia cells in vitro. By virtue of these properties, neural stem cells and their progeny can be applied for pharmaceutical drug discovery and for cell transplantation in neurological disorders.

The fate of neural stem cells can be controlled by a variety of extracellular factors. Growth factors such as basic Fibroblast Growth Factor (bFGF), Epidermal Growth Factor (EGF), Transforming Growth Factor (U.S. Pat. Nos. 5,851, 832 and 5,753,506) and Leukemia Inhibitory Growth Factor (LIF; U.S. Pat. No. 6,103,530 to Carpenter) have all been shown to control the in vitro proliferation of neural stem cells. Growth factor expanded stem cells can differentiate into neurons and glia after mitogen withdrawn from the culture medium, but the proportion of neural stem cells that differentiate into neurons is minimal. However, the proportion of neural stem cells differentiating into the neuronal pathway can be increased by exposing the neural stem cells to various other growth factors such as Platelet Derived Growth Factor (PDGF; U.S. Pat. No. 5,753,506); bFGF (U.S. Pat. No. 5,766,948 to Gage and Jasodha); Brain Derived Growth Factor (BDNF; Shetty and Turner, J Neurobiol. 1998;35:395–425); including neurotrophins such as Neurotrophin-3 (NT-3) and Neurotrophin-4 (NT-4; Caldwell et al., Nat Biotechnol. 2001;19:475–9); Notch antagonists (U.S. Pat. No. 6,149,902 to Artavanis-Tsakonas et al.), retinoic acid (U.S. Pat. No. 6,395,546 to Zobel et al.; or BMP-2 (U.S. Pat. Nos. 5,948,428 to Lee et al., and 6,001, 654 to Anderson et al.) to increase the quantity of neurons derived from a certain amount of neural stem cells.

The antiepileptic drug valproate (VPA) or valproic acid (n-dipropylacetic acid), a simple branched-chain carboxylic acid, is an established human teratogen, (i.e., an agent capable of causing malformations in embryos), which affects neural development in human fetuses exposed to the drug during early pregnancy. In vitro cellular models have been used to investigate the teratogenic effect of valproate and its structural analogs, mainly by use of tumor cell lines (Courage-Maguire et al., Int J Dev Neurosci 1997; 15:37–43). In such studies, valproate has been found to inhibit the proliferation and block retinoic acid-induced neuronal differentiation of the teratocarcinoma cell line NTera-2 (Skladchikova et al., Neurotoxicol. 1998;19:357–70). By contrast, in a neuroblastoma cell line, the antiproliferative effect of valproate appeared to be associated with cell differentiation, as an increase of neuronal morphology and neural cell adhesion molecule expression was observed after exposure to valproate (Cinatl et al., Anticancer Drugs 1996;7:766–73; Slesinger and Singer, Epilepsia 1987; 28:214–21; Knupfer et al., Anticancer Res 1998; 21:347–51; Yuan et al, J Biol Chem 2001; 276: 31674–83). The reported effect of valproate on maturation in these studies was always associated with an inhibition of cell proliferation. Similar effects of valproate have been found in other tumors (Slesinger and Singer, Epilepsia 1987; 28:214–21; Knupfer et al., Anticancer Res 1998; Gottlicher et al., Embo J 1998; 20:6969–78). In a recent study, valproate was also shown to increase the cytoprotective protein bcl-2 in the brain and neurite outgrowth in vitro (Manji et al., Biol Psychiatry 2000;48:740–54), indicating that valproate may have a neurotrophic effect on already differentiated neuronal cells, i.e., to inhibit apoptosis and promote maturation of neurons. Finally, valproate has been suggested to serve as a neurotrophic factor and an anti-proliferative compound on tumorigenic and primary neuronal cell lines (U.S. Pat. No. 5,672,746 to Nau et al.). There have been no reported results showing that valproate induces neuronal differentiation without inhibiting proliferation.

The availability of large quantities of neuronal cells such as neurons or neuroblasts is important for the application of such cells both in vivo and in vitro, e.g., in cell transplantation therapy for neurodegenerative diseases and in vitro drug testing in psychiatric disorders. Such quantities can only be obtained by differentiation of cultured neural stem cells into these cell types, which requires large-scale cell culture using a significant amount of various growth factors and/or neurotrophins. Given the sparse availability of neural stem cells, especially human neural stem cells, and the cost of growth factor and neurotrophin preparations, there is a need for more efficient and economically viable strategies for differentiating neural stem cells into neuronal cells such as neuroblasts and neurons. This invention addresses these and other needs in the art.

SUMMARY OF THE INVENTION

The present invention is based on the surprising discovery that valproate can be used for efficient differentiation of bFGF-expanded multi-potent neural stem cell or pluripotent progenitors or such cells capable of differentiating into neurons and neuroblasts. Accordingly, the present invention provides a method for promoting differentiation of neural stem cells into a neuronal cell such as a neuroblast or a neuron, comprising contacting the neural stem cell with valproate or analogs thereof.

In one embodiment, the neural stem cell is exposed to valproate at a concentration in the range of about 1 nM to about 1M, for a period of about 1 h to about 30 days. Preferably, the concentration of valproate is about 1 mM, and the neural stem cell exposed to valproate daily for a period of about 6 days. In another preferred embodiment, the concentration of valproate is about 1 mM, and the neural stem cell exposed to valproate daily for a period of about 2 days. In a third preferred embodiment, the concentration of valproate is 1 mM and the exposure is 6 days.

The present invention also provides for a method of promoting differentiation of neural stem cells into neuronal cells by contacting the neural stem cell not only with valproate but also with one or more of the vitamin A metabolite 9-cis retinoic acid (9-cis RA) and neuronal conditioned medium (NCM). In one embodiment, the concentrations of 9-cis retinoic acid is 1 nM and the NCM is used in an amount sufficient to further promote neuronal differentiation. In one embodiment, the NCM is diluted to a 0.5× dilution.

The present invention also contemplates methods of treating CNS or PNS disorders characterized by neuronal damage in a mammal by administering valproate to individuals in need thereof, or by transplantation of neurons that have been differentiated with valproate in culture to individuals in need thereof.

The present invention further provides methods of screening for drugs that affect neuronal differentiation, or for producing highly differentiated neurons from stem cells. A culture with a high proportion of differentiated neurons derived from human stem cells can reproduce, to a certain extent, the degree of complexity of the human brain. These cultures can be used for drug screening for molecules that affect not only differentiation but also gene expression in CNS or PNS disorders involving neuronal damage or depletion. In the latter case, molecules identified can be used as lead compounds or new drug candidates to restore the expression of genes associated with the disorder to that of healthy neurons, or to bring it closer to that of healthy neurons).

In a related and more detailed aspect, the invention provides methods for screening for such molecules employing (i) a culture of stem cells derived from a primary culture of stem cells from an individual suffering from such a CNS or PNS disorder, and differentiating said culture using valproate alone or in combination with other differentiating agents; and (ii) a culture of stem cells derived from a primary culture of stem cells from an individual suffering from such a CNS or PNS disorder.

In another related and more detailed aspect, the invention provides a method for screening for such molecules based on genes having different levels of expression in healthy and affected neurons which are associated with such disorders. Restoration of the expression level of one or more of such genes to (or close to) that of healthy neurons qualifies the test compound as a lead compound or new drug candidate.

Additional preferred aspects of the invention can be gleaned from the claims, the independent ones among them are incorporated by reference.

BRIEF DESCRIPTION OF THE DRAWINGS

This patent or application file contains at least one drawing executed in color. Copies of this patent or patent application publication with color drawing(s) will be provided by the Office upon request and payment of the necessary fee.

FIG. 2B shows that valproate increases β tubulin-III expression in rat cortical stem cells. Western blots analysis of β tubulin-III expression was performed on cell extracts from rat cortical stem cells treated with valproate for 1 day.

DETAILED DESCRIPTION OF THE INVENTION

Figure 1A:
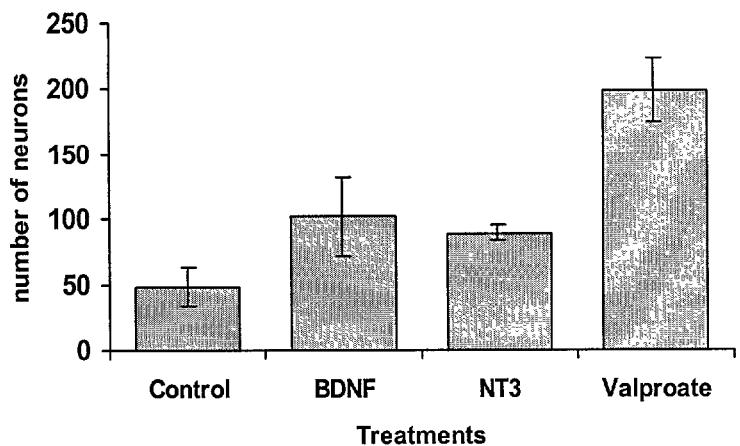
FIG. 1A. This figure shows that valproate treatment increases the number of neurons derived from neural stem cells compared to controls and cells exposed to neurotrophins or growth factors. Rat cortical stem cell cultures were treated for 6 days with either valproate, BDNF or NT-3. Neurons were identified via detection of the expression of β tubulin-III using immunofluorescence. Results represent the number of neurons per field. Results are shown from one representative experiment out of six. Three wells and four representative fields per well were counted.

According to the present invention, mammalian neural stem cell differentiation can be stimulated by exposing the cells to valpro ate. Valproate is a small and inexpensive compound, readily available from commercial sources, which in contrast to most growth factors is stable in solution. In addition, the activity of valproate could be relatively easily improved by using valproate enantiomers (pentanoic acid derivatives), analogs, or other structurally related molecules. The activity of these new candidate molecules can be rapidly and easily screened for their efficacy on the proliferation and neuronal differentiation of neural stem cells.

The capacity to efficiently differentiate neurons is important both for the treatment of neurodegenerative diseases and in vitro studies of cells to be used in transplantation, or to be used for research and drug screening processes in pharmaceutical industries. Neural stem cells provide the ideal in vitro system to study neuronal differentiation. However, very few systems for efficient neuronal differentiation, whether in vivo or in vitro, have been found so far. The instant invention enables the differentiation of neurons of choice from stem cells originating from different regions of the brain. Furthermore, while most differentiation protocols so far have used exclusively growth factors, the invention offers a novel and economically advantageous concept in the field; the use of a small molecule that can promote neuronal differentiation.

As shown in the Examples, valproate promotes neural stem cell differentiation into neurons. Moreover, the differentiation-promoting effect of valproate is higher than that of BNDF, a known promoter of neural stem cell differentiation (Shetty and Turner, J Neurobiol. 1998;35:395–425), and NT-3. One reason why valproate increases neuronal differentiation more potently than these other factors is that although valproate effectively differentiate neural stem cells into neuronal cells, valproate does not inhibit, but can stimulate the proliferation of neural stem cells. This is a novel and unexpected finding, since the results from previous investigations on valproate (see supra) suggested that this drug promoted cell differentiation by inhibiting proliferation of the tumor cell lines studies. Thus, unexpectedly, valproate promotes differentiation of neural stem cells via a novel mechanism that does not inhibit proliferation.

The present invention also demonstrates that valproate enhances neuronal differentiation potentiated by other differentiation agents, namely 9-cis retinoic acid with neural conditioned medium.

This novel differentiation mechanism of valproate and analogs thereof will identify new molecular targets in the pathways regulating neuronal fate. Most of the growth factors (BDNF, NT-3, NT-4, bFGF, PDGF) known to date to improve the proportion of neurons differentiating from neurons act on specific receptors linked to tyrosine kinase. To date, no studies have indicated that tyrosine kinase receptors are involved in the action of valproate. New functional genomic technology can be used to identify the molecular cascade associated with the neuronal fate induction of valproate on neural stem cells.

Definitions

The terms used in this specification generally have their ordinary meanings in the art, within the context of this invention and in the specific context where each term is used. Certain terms are discussed below, or elsewhere in the specification, to provide additional guidance to the practitioner in describing the compositions and methods of the invention and how to make and use them.

As used herein, the term "about" or "approximately" means within 50%, preferably 25%, more preferably 10%, and most preferably 5% of the given value. Alternatively, the term "about" means the standard deviation or variance for a given value, if available.

"Differentiation" is intended to encompass a process whereby a relatively unspecialized cell, e.g., a neural stem cell, acquire a specialized structural and/or functional feature that characterize a cell, tissue, or organ of a mature organism, or during a particular developmental phase if an organism. Examples of structural features include the expression of marker molecules by the cell, which may be identified using immunohistochemical staining procedures known in the art. In particular, antibodies specific for various neuronal or glial proteins may be employed to identify phenotypic properties of the differentiated cells.

The term "stem cell" refers to a cell that has the capacity to spontaneously differentiate into two or more subtypes of cells. A stem cell is capable of division to produce daughter cells that can be either new stem cells or further differentiated cells. Preferably, the stem cell is capable of self-maintenance, meaning that with each cell division, one daughter cell will also be a stem cell. A "totipotent" stem cell is capable of differentiating into all tissue types, including cells of the meso-, endo-, and ectoderm. A "multipotent" stem cell is a cell which is capable of differentiating into at least two of several fates.

A particular type of multipotent stem cell is a "neural stem cell", which is a stem cell of the nervous system that is capable of differentiating into neurons, and glia (including oligodendrocytes, and astrocytes). A neural stem cell is a multipotent stem cell which is capable of multiple divisions, and under specific conditions can produce daughter cells which are neural stem cells, or neural progenitor cells that can be neuroblasts or glioblasts, i.e. cells committed to become one or more types of neurons and glial cells respectively. Markers indicating that a cell is a neural stem cell include nestin. Generally, a neural stem cell does not express the following markers: neurogenin, neuron specific enolase ("NSE"), neurofilament, tau, $\beta$ tubulin III, microtubule-associated protein 2a and b (MAP-2), Neu N, HuD (RNA binding protein), GFAP, Galactocerebroside, O4, and myelin proteins.

A "progenitor cell" or "precursor cell", used interchangeably herein, is a stem cell progeny that is committed to a particular differentiation pathway. A progenitor/precursor cell has the capability to proliferate, but to a more limited degree than a stem cell. For example, a particular type of progenitor cell is a "neuroblast", which is committed to becoming a neuron but is not yet a mature neuron. Other types of progenitor/precursor cells derived from neural stem cells include cells committed to the glial pathway, i.e., astroblasts, which are committed to becoming astrocytes (type I and type II); and bipotent precursors that can become either neurons or astrocytes, neurons or oligodendrocytes, or oligodendrocytes or astrocytes. Schwann cells and oligodendrocytes differentiate from the latter cell types.

A "neuron" is a cell which is the progeny of or derived from a neuroblast, a bipotent precursor and/or a neural stem cell. A neuron can be post-mitotic, i.e., non-proliferative. For example, a neuroblast or progenitor cell can convert directly into a neuron, or proliferate in the presence of a mitogen (e.g., bFGF) and then convert into a postmitotic neuron. Neurons are specialized for the transmission of nerve impulses. Each neuron consists of an enlarged portion, the cell body or perikaryon containing the nucleus and from which a variable number of thread-like processes, called dendrites, project. A neuron may also contain a single nerve fiber or axon which conveys impulses away from the body. Neurons may be identified using visual inspection or immunohistochemistry with antibodies to neuron specific enolase ("NSE"), neurofilament, tau, β-tubulin III, microtubule-associated protein 2A and B (MAP-2), Neu N, HuD (RNA binding protein) or other known neuronal markers. Generally, neurons are nestin-negative.

The central nervous system or CNS the part of the nervous system which in vertebrates consists of the brain and spinal cord, to which sensory impulses are transmitted and from which motor impulses pass out, and which supervises and coordinates the activity of the entire nervous system.

The peripheral nervous system or PNS is the part of the nervous system that is outside the central nervous system and comprises the cranial nerves excepting the optic nerve, the spinal nerves, and the autonomic nervous system. A disorder affecting the neurons within the CNS or PNS is a "neurological disorder."

The term "psychiatric disorder" or "neuropsychiatric disorder", which may also be referred to as a "major mental illness disorder" or "major mental illness", refers to a disorder which may be generally characterized by one or more breakdowns in the adaptation process. Such disorders are therefore expressed primarily in abnormalities of thought, feeling and/or behavior producing either distress or impairment of function (i.e., impairment of mental function such with dementia or senility). Currently, individuals may be evaluated for various neuropsychiatric disorders using criteria set forth in the most recent version of the American Psychiatric Association's Diagnostic and Statistical Manual of Mental Health (DSM-IV). Exemplary psychiatric disorders include, but are not limited to, schizophrenia, attention deficit disorder (ADD), schizoaffective disorder, bipolar disorder, bipolar affective disorder, unipolar affective disorder, adolescent conduct disorder, autism, depression, and anxiety disorders.

A "neurodegenerative disease" is a disease which progressively degenerates neurons or neuronal function. Examples of neurodegenerative diseases include all forms of senile dementia including chronic disorders such as Alzheimer's disease and Huntington's Chorea, Parkinson's disease, amyotrophic lateral sclerosis, and acute disorders such as stroke, schizophrenia, epilepsy, and injury of the brain, peripheral nerves or spinal cord.

A mammal refers to any of the higher vertebrate animals comprising the class Mammalia, including but not limited to humans and non-human animals.

"Non-human animals" include, without limitation, laboratory animals such as mice, rats, rabbits, hamsters, guinea pigs, etc.; domestic animals such as dogs and cats; and, farm animals such as sheep, goats, pigs, horses, and cows. A non-human animal of the present invention may be a mammalian or non-mammalian animal; a vertebrate or an invertebrate.

Valproate or valproic acid (CAS Registry No. 99-66-1) is also known as Dalpro; Depakote; Myproic acid; 2-Propyl-pentanoic acid; Propylvaleric acid; Dipropylacetic acid; Mylproin; di-n-propylacetic acid; n-dipropylacetic acid; 2-propylvaleric acid; 4-heptanecarboxylic acid; Abbott 44090; 2,2-Di-n-propylacetic acid; di-n-Prophylacetic acid; Convulex; Epicon; Leptilan; Valporal; and Vistora. As used herein, the term includes physiologically acceptable salts such as sodium valproate.

Valproate analogs that have also been shown to inhibit proliferation and enhance differentiation, and have been show to have in vivo teratogenic activity included, 2-ethylhexanoic acid, 2-propylhexanoic acid, 2-butylhexnoic acid, and (s)-4-yn-valproate (Courage-Maguire et al., it J Dev Neurosci 1997; 15:37–43; Maar et al., Toxicology 1997; 116:159–68; Werling et al., Mol Pharmacol 2001; 59:1269–76). Non-teratogenic analogs that have not been shown to affect differentiation include R-4-yn-valproate, 2-en-valproate and 4 methyl-valproate (Maar et al., Toxicology 1997; 116:159–68; Werling et al., Mol Pharmacol 2001; 59:1269–76).

9-cis retinoic acid (9cRA; CAS Registry No. 5300-03-8), is a geometric isomer of all-trans-retinoic acid (RA). It is an endogenous high-affinity ligand for retinoid X receptors and retinoic acid receptors and activates them with high potency. Retinoic acids are metabolites of vitamin A that play a role in the differentiation and proliferation of numerous normal and transformed cell types. Retinoic acid has been demonstrated to indirectly modulate differentiation of neurons through the modification of expression of neuronal cell surface receptors to peptide growth factors (Scheibe, R. J. and Wagner, J. A., J. Biol. Chem. 1992; 267, 17611).

Gamma Aminobutyric Acid (GABA) refers to the major inhibitory neurotransmitter in the mammalian CNS. GABA participates in the regulation of neuronal excitability through interaction with specific post-synaptic GABAA receptors. Binding of GABA to these postsynaptic receptors, results in an opening of a chloride channel integrated in the receptor which allows the entry of Cl— and consequently leads to hyperpolarization of the recipient cell.

The phrase "pharmaceutically acceptable" refers to molecular entities and compositions that are "generally regarded as safe", e.g., that are physiologically tolerable and do not typically produce an allergic or similar untoward reaction, such as gastric upset, dizziness and the like, when administered to a human. Preferably, as used herein, the term "pharmaceutically acceptable" means approved by a regulatory agency of the Federal or a state government or listed in the U.S. Pharmacopeia or other generally recognized pharmacopeia for use in animals, and more particularly in humans. Physiologically acceptable means any solvent or solution consisting of components that are physiological and non-toxic, such as buffered salt solutions. The term "carrier" refers to a diluent, adjuvant, excipient, or vehicle with which the compound is administered. Such pharmaceutical carriers can be sterile liquids, such as water and oils, including those of petroleum, animal, vegetable or synthetic origin, such as peanut oil, soybean oil, mineral oil, sesame oil and the like. Water or aqueous solution saline solutions and aqueous dextrose and glycerol solutions are preferably employed as carriers, particularly for injectable solutions. Suitable pharmaceutical carriers are described in "Remington's Pharmaceutical Sciences" by E. W. Martin.

The term "effective dose" refers to that amount of a compound or compositions that is sufficient to result in a desired activity. Thus, and effective dose of a valproate would be the dose sufficient to induce differentiation of neural stem cells to express preferentially a neuronal phenotype. For a substance administered to a subject, a "effective amount" for administration is that creating a sufficient concentration of the active ingredient or a metabolite thereof at the target site e.g., in the vicinity of a neural stem cell of said subject.

In accordance with the present invention, there may be employed conventional molecular biology, microbiology and recombinant DNA techniques within the skill of the art. Such techniques are explained fully in the literature. See, for example, Sambrook, Fitsch & Maniatis, Molecular Cloning: A Laboratory Manual, Second Edition (1989) Cold Spring Harbor Laboratory Press, Cold Spring Harbor, N.Y. (referred to herein as "Sambrook et al., 1989"); DNA Cloning: A Practical Approach, Volumes I and II (D. N. Glover ed. 1985); Oligonucleotide Synthesis (M. J. Gait ed. 1984); Nucleic Acid Hybridization (B. D. Hames & S. J. Higgins, eds. 1984); Animal Cell Culture (R. I. Freshney, ed. 1986); Immobilized Cells and Enzymes (IRL Press, 1986); B. E. Perbal, A Practical Guide to Molecular Cloning (1984); F. M. Ausubel et al. (eds.), Current Protocols in Molecular Biology, John Wiley & Sons, Inc. (1994).

In addition, various methods for culture and differentiation of CNS cells may be used in accordance with the present invention. Such methods are also explained fully in the literature. See, for example, "Protocols For Neural Cell Culture", (Federoff and Richardson, eds., Humana Press, Totova, N.J., 1997) and "Culturing Nerve Cells (Banker and Goslin, eds., the MIT Press, Cambridge, Mass., 1998).

Preparation and Expansion of Neural Stem Cells

Multipotent neural stem cells can be obtained from embryonic, fetal, post-natal, juvenile or adult neural tissue. The neural tissue can be obtained from any animal that has neural tissue such as insects, fish, reptiles, birds, amphibians, and mammals. The preferred source of neural tissue is from mammals, preferably rodents and primates, and, most preferably, rats and humans.

Typically, extracted neural tissue sample is placed into an appropriate medium such as HBSS without divalent cations, buffered with HEPES and sodium bicarbonate-see Methods below. Next, tissue is dissociated into cells using enzymatic techniques (e.g., trypsinization) or gentle mechanical dissociation (e.g., trituration). The dissociated cells can then be cultured as neurospheres or as a monolayer using a suitable growth medium. For example, cells can be cultured in NSA (Euroclone, UK) or DMEM/F12 medium (described infra) complemented with one or more growth factors such as, e.g., basic fibroblast growht factor (bFGF), epidermal growth factor (EGF), transforming growth factor-alpha (TGFα), transforming growth factor-beta (TGFβ), and leukocyte inflammatory factor (LIF). In the case of monolayer culture, cells may be grown in the presence of bFGF on a plastic surface or in a dish pre-coated with a substrate to which the cells can attach. Such substrates include, but is not limited to, poly-ornithine and fibronectin. At regular intervals, the cells should be subcultivated or split to ensure a suitable cell density.

Differentiation of Neural Stem Cells

Neural stem cells can be differentiated into neurons using the method of the invention, i.e., contacting the neural stem cells with valproate or analogs. Differentiation of a neural stem cell may be accomplished as follows. First, culture medium containing cell growth promoting factors should be replaced with a medium which does not contain mitogens or growth factors etc., i.e., a "differentiation medium." In a preferred embodiment, this medium is serum-free medium supplemented with insulin, transferin, selenium and/or steroids. Next, valproate is added to the differentiation medium. In an alternative embodiment, the valproate is already present in the differentiation medium. In one embodiment, the neural stem cell is exposed to valproate or a valproate analog at a concentration in the range of about 1 pM to about 1M, even more preferably in the range of 1 nM to 10 mM, for a period of about 1 h to about 10 days. In a preferred embodiment, the concentration of valproate is in the range of about 0.01 to about 10 µM, or, even more preferably, about 0.1 or 1 mM. In another preferred embodiment, brain-derived neurotrophic factor (BDNF) is also present in or added to the differentiation medium. The preferred concentration range of BDNF is from about 10 pg/ml to about 10 µg/ml, more preferably, the concentration of BDNF is about 20 ng/ml. In yet another preferred embodiment, the neural stem cell is exposed to valproate for a period of about 1 to about 10 days, preferably about 6 days. In another embodiment, neuronal conditioned medium and 9-cis Retinoic acid are also added to the differentiation medium with valproate. The preferred concentration range of 9-cis Retinoic Acid is from about 1 nM to 1 mM, more preferably, 1 nM.

Preferably, the method of the invention provides neural stem cell cultures comprising at least about 30%, more preferably at least about 40%, and most preferably at least about 50% neuroblasts or neurons differentiated from a mammalian neural stem cell culture.

Evaluation of Neural Stem Cell Differentiation

Neural stem cell differentiation into a neuroblast or a neuron can be analyzed by either immunohistochemical techniques or visual inspection to assess the number of neuronal cells or neurons formed after conducting a differentiation assay. Alternatively, the relative proportion of neuronal cells, neuroblasts, or neurons to remaining neural stem cells, or total number of cells, may be estimated. For example, neural stem cells may be identified using immunohistochemistry with antibodies specific for a marker such as, e.g., nestin, and neurons may be identified using antibodies for neuron-specific markers such as, e.g., β-tubulin, NSE, neurofilament, tau, microtubule-associated protein 2a and 2b, Neu N, neurogenin, or other markers known in the art.

Applications

As described herein, the present invention provides a method to promote the differentiation of neural stem cells, preferably mammalian neural stem cells, into neurons employing valproate or analogs. The invention also provides cell cultures enriched in neurons as compared to control cultures.

Neural stem cells provide the ideal in vitro system to prepare neuronal cells and to study neuronal differentiation. However, very few systems for efficient neuronal differentiation, whether in vivo or in vitro, have been found so far. The instant invention enables the differentiation of neurons of choice from stem cells originating from different regions of the brain. Furthermore, while most differentiation protocols so far have used exclusively growth factors, the invention offers a novel and economically advantageous concept in the field; the use of a small molecule that can promote neuronal differentiation.

The method to promote neuronal differentiation, and the differentiating or differentiated cells themselves, can be used for any purpose or application in which neuronal differentiation or a cell population enriched in neurons is desired. This section describes some exemplary application areas, such as in drug screening assays, and treatment of CNS disorders.

Drug Screening

For drug screening purposes, the method of the invention can be used, for example, to identify agents which modify the gene expression of differentiating or differentiated neurons, or which modify valproate-mediated differentiation of neural stem cells. These assays can be conducted in vitro or in vivo model systems, using mice or other animals, or cultures of cells derived from neural stem cells.

Gene Expression Assays. Changes in gene expression associated with CNS disorders such as neuropsychiatric disorders or neurodegenerative disorders can provide significant insights into pathways of disease etiology or drug action, and also help identify novel targets for drug screening. Once a gene or a set of genes are known that are differentially expressed in a disease or disorder, and a correlation is established between a gene or a set of genes and a disease or disorder, defining a "disease signature", screening programs for drugs that revert the "disease signature" to a normal (or close-to-normal) expression pattern can be initiated even when the functions of an individual gene are not fully understood. The screening methods can use cultured cells to screen for candidate drug compounds or lead compounds. Preferably, the cells are ones having an expression profile that is typical of neuronal cells or, alternatively, they may be neuronal cells manipulated to produce an expression profile typical of cells of a particular CNS disorder. In a preferred embodiment, the cells are neurons that have been differentiated from neural stem cells using valproate. The cells or cell lines used will also, preferably, give rise to reproducible changes in their gene expression profiles when contacted with known therapeutic drugs used to treat CNS disorders, such as antipsychotic drugs. In particularly preferred embodiment, these changes will be opposite changes that are observed in the disease signature. That is to say, in such embodiments genes (or their homologs) that are normally expressed at higher levels in the disease signature are preferably expressed at lower levels in cells or cell lines contacted with the known antipsychiatric drug, and vice-versa.

When a large number of drugs are to be screened for such a purpose, a high-throughput assay where the effect of many drugs on living cells are assessed simultaneously is a major advantage. In the prior art, however, these types of assays have been largely impeded by the lack of a reproducible source of large quantities of neuronal cells particularly neurons having normal gene signatures or in which gene signatures mimicking "disease signatures" can be implemented. These problems can now be addressed using the method of the invention.

One exemplary screening method contemplated for use in this invention is multi-parameter high-throughput screening, or MPHTS. This method is described in U.S. Provisional Application Ser. No. 60/349,936, filed Jan. 18, 2002, and U.S. non-provisional application Ser. No. 10/175,523, filed Jun. 18, 2002, entitled Multiple Parameter High-Throughput Screening (MPHTS), commonly owned, both hereby incorporated by reference in their entirety. MPHTS can advantageously be used for screening for drugs or compounds that affect gene expression in neural cells to identify compounds that affect the disease signatures of CNS, neuropsychiatric, neurodegenerative, and/or other neurological disorders. Generally, an MPHTS assay based on cultures cells can involve the following gene expression systems.

First, as described above, "disease-signatures" are obtained or provided by measuring expression levels for a plurality of genes in cells or tissues derived from an individual having a neuropsychiatric disorder. In some instances, "disease-signatures" may be also created in cultured cells in vitro, by manipulating cultured normal cells to exhibit a known "disease signature".

Second, "normal" gene-signatures can be obtained or provided by measuring expression levels for a plurality of genes in cultured neuronal cells (e.g., in cultured neurons that are derived from neural stem cells differentiating or differentiated according to the method of the present invention). Thereby, the "disease-signatures" can be compared to expression levels in normal cells or tissues (i.e., brain cells or tissues from healthy individuals, not affected by a CNS disorder) to identify the particular genes that are differentially expressed in the CNS disorder of interest.

Third, "drug signatures" may also be obtained or provided by measuring expression levels for a plurality of genes in cultured neuronal cells or tissues that are treated with a therapeutic compound known to be effective for treating a CNS disorder. Exemplary drug signatures, which were obtained from both rat and human neuronal cells treated with therapeutic compounds, are provided in U.S. provisional patent application Ser. No. 60/349,936, filed Jan. 18, 2002, and U.S. non-provisional application Ser. No. 10/175,523, filed Jun. 18, 2002, entitled Multiple Parameter High-Throughput Screening (MPHTS), commonly owned, both hereby incorporated by reference in their entirety. Other drug signatures may be readily obtained by those skilled in the art.

Fourth, expression levels for the plurality of genes are obtained or provided in neuroblasts or neurons that are contacted with a test compound, i.e., "drug candidate signatures", and these expression levels may then be compared to "disease signatures" and/or to "drug-signatures".

Generally speaking, the "drug candidate signature" is compared to the "normal" gene signatures to identify changes in the expression level(s) for particular genes. Similarly, the "drug-signature" is also compared to the "normal" gene signature, to identify particular genes whose expression levels change when the cells are contacted with the known therapeutic compound. Compounds that are determined to affect changes in the expression levels of particular genes are designated "lead compounds." In instances where changes in expression levels when the cells are contacted with the test compound are identical (or at least similar) to changes in expression levels when the cell are contacted with the known therapeutic compound, then the test compound is identified as a "drug candidate" compound for treating the CNS disorder. Thus, using these screening methods a skilled artisan is able to rapidly and inexpensively identify compounds that are most promising as novel drugs for treating CNS disorders, while eliminating compounds that show little promise and/or are unlikely candidates for this purpose.

In addition, the "drug-candidate signature" may also be compared to the "disease signature". Preferred drug candidates are those which alters the expression of "signature gene" in a way that is opposite or contrary to the expression observed in the disorder's gene signature. For example, where a particular gene is expressed at abnormally high levels in cells or tissues from individuals affected by the particular CNS disorder (compared to expression levels in cells or tissues from individuals not affected by the disorder), a candidate compound identified in these screening methods will preferably inhibit that gene's expression (i.e., the gene is preferably expressed at lower levels when the cells are contacted with the test compound, compared to its expression when the cell is not contacted with the test compound).

Differentiation Assays. In one particular embodiment, the screening assays is designed to screen for compounds that affect valproate-induced differentiation of neural stem cells. The assay can, for example, be based on genes that are specifically expressed in differentiating neural stem cells, and identify compounds which affect the expression of these genes. Alternatively, the assays can identify phenotypic changes in differentiating cells such as the expression of antigens typical of specific types of cells (see above). In a specific embodiment, the method can identify a compound that affects differentiation of mammalian neural stem cells by (a) exposing a first population of cultured multipotent or pluripotent neural stem cells to valproate in an amount sufficient to induce differentiation of said cells preferentially into neurons in the presence of a test compound, which test compound can be added before or after the valproate (b) exposing a second population of multipotent or pluripotent neural stem cells to the same amount of valproate in the absence of the test compound, and comparing the portion of neurons resulting in step (a) to the portion of neurons resulting in step (b). If a difference is found, the test compound affects neuronal differentiation and is a "lead compound."

Any screening technique known in the art can be used to screen for compounds that modulate valproate-induced neuronal differentiation, including gene expression techniques. The present invention contemplates screens for synthetic small molecules as well as screens for natural molecules that agonize or antagonize the activity of differentiation in vivo. For example, natural products libraries can be screened using assays of the invention for molecules that agonize or antagonize plasma cell activity.

Gene Expression Evaluation. Gene expression evaluation technologies, such as differential display and subtractive hybridization methods, can be used in the present invention to ascertain genes that are expressed or turned off in differentiated or differentiating neural stem cells, such as subtractive hybridization (see, e.g., U.S. Pat. No. 5,700,644, issued to Gould et al. and U.S. Pat. No. 5,665,547, issued to Pardee et al.). In addition, oligonucleotide expression array technology can be used to evaluate gene expression, and to identify gene expression that either correlates with or is distinct from gene expression in diseased neurons (see, e.g., Little et al., Genet. Anal. 6:151, 1996).

By way of example, GeneChip expression analysis (Affymetrix, Santa Clara, Calif.) generates data for the assessment of gene expression profiles and other biological assays. Oligonucleotide expression arrays simultaneously and quantitatively interrogate thousands of mRNA transcripts (genes or ESTs), simplifying large genomic studies. Each transcript can be represented on a probe array by multiple probe pairs to differentiate among closely related members of gene families. Each probe cell contains millions of copies of a specific oligonucleotide probe, permitting the accurate and sensitive detection of low-intensity mRNA hybridization patterns. After hybridization intensity data is captured, e.g., using a Hewlett-Packard GeneArray™ scanner, software can be used to automatically calculate intensity values for each probe cell. Probe cell intensities can be used to calculate an average intensity for each gene, which directly correlates with mRNA abundance levels. Expression data can be quickly sorted on any analysis parameter and displayed in a variety of graphical formats for any selected subset of genes. Other gene expression detection technologies include the research products manufactured and sold by Perkin-Elmer and Gene Logic.

Test compounds. As used herein, the term "test compound" refers to any protein or polypeptide, nucleic acid (such as an antigens or ribosome nucleic acid), or small molecule compound, including steroid hormone, arachidonic acid metabolite (leukotriene or prostaglandin), small peptide hormone (e.g., an opioid), or synthetic organic molecule.

Antigens nucleic acids (including ribozymes), may be used to inhibit expression of one or more specific proteins in order to modulate neuronal differentiation. Such antigens nucleic acids can be tested using the present invention for in vivo activity. An "antigens nucleic acid" is a single stranded nucleic acid molecule which, on hybridizing under cytoplasmic conditions with complementary bases in an RNA or DNA molecule, inhibits the latter's role. If the RNA is a messenger RNA transcript, the antigens nucleic acid is a counter transcript or mRNA-interfering complementary nucleic acid. As presently used, "antigens" broadly includes RNA-RNA interactions, RNA-DNA interactions, ribozymes and RNase-H mediated arrest. Antigens nucleic acid molecules can be encoded by a recombinant gene for expression in a cell (e.g., U.S. Pat. No. 5,814,500; U.S. Pat. No. 5,811,234), or alternatively they can be prepared synthetically (e.g., U.S. Pat. No. 5,780,607).

Classes of compounds that may be identified by such screening assays include, but are not limited to, small molecules (e.g., organic or inorganic molecules or peptides which are less than about 2 kD in molecular weight, are more preferably less than about 1 kD in molecular weight, and/or are able to cross the blood-brain barrier or gain entry into an appropriate cell, as well as macromolecules (e.g., molecules greater than about 2 kD in molecular weight). Compounds identified by these screening assays may also include peptides and polypeptides. For example, soluble peptides, fusion peptides members of combinatorial libraries (such as ones described by Lam et al., Nature 1991, 354: 82–84; and by Houghten et al., Nature 1991, 354:84–86); members of libraries derived by combinatorial chemistry, such as molecular libraries of D- and/or L-configuration amino acids; phosphopeptides, such as members of random or partially degenerate, directed phosphopeptide libraries (see, e.g., Songyang et al., Cell 1993, 72:767□–778); antibodies, including but not limited to polyclonal, monoclonal, humanized, anti□-idiotypic, chimeric, or single chain antibodies; antibody fragments, including but not limited to FAb, F(ab')2, FAb expression library fragments and epitope-binding fragments thereof.

One approach uses recombinant bacteriophage to produce large libraries. Using the "phage method" (Scott and Smith, Science 249:386–390, 1990; Cwirla, et al., PNAS USA 87:6378, 1990; Devlin et al., Science, 49:404, 1990), very large libraries can be constructed (106–108 chemical entities). A second approach uses primarily chemical methods, of which the Geysen method (Geysen et al., Molecular Immunology 23:709, 1986; Geysen et al. J. Immunologic Method 102:259, 1987; and the method of Fodor et al. (Science 251:767, 1991) are examples. Furka et al. (14th International Congress of Biochemistry, Volume #5, Abstract FR:013, 1988; Furka, Int. J. Peptide Protein Res.

37:487–493, 1991), Houghton (U.S. Pat. No. 4,631,211, issued December 1986) and Rutter et al. (U.S. Pat. No. 5,010,175, issued Apr. 23, 1991) describe methods to produce a mixture of peptides that can be tested as agonists or antagonists.

In another aspect, synthetic libraries (Needels et al., Proc. Natl. Acad. Sci. USA 90:10700–4, 1993; Ohlmeyer et al., PNAS USA 90:10922, 1993; Lam et al., International Patent Publication No. WO 92/00252; Kocis et al., International Patent Publication No. WO 9428028) and the like can be screened for molecules that have CNS or PNS activity restorative of abnormal expression of genes within a gene signature.

The compounds used in such screening assays are also preferably essential pure and free of contaminants that may, themselves, alter or influence gene expression. Compound purity may be assessed by any number of means that are routine in the art, such as LC-MS and NMR spectroscopy. Libraries of test compounds are also preferably biased by using computational selection methods that are routine in the art. Tools for such computational selection, such as Pipeline Pilot™ (Scitegic Inc., San Diego, Calif.) are commercially available. The compounds may be assessed using rules such as the "Lipinski criteria" (see, Lipinski et al., Adv. Drug Deliv. Rev. 2001, 46:3–26) and/or an other criteria or metrics commonly used in the art.

In summary, the method of the invention can be applied for large-scale preparations of complex systems (including neurons) for the screening of compounds in high-throughput screens for drug candidates and for gene discovery purposes. As discussed above, the generation of primary neuronal cultures from human central nervous system has been problematic because of the limited availability of post-mortem, and even less of live tissue, from which to make such cultures. Thus, the present invention provides an alternative method by which these cultures may be generated. Neural stem cells are a better source of primary human cultures than post-mortem tissues or live tissues, because they are capable of dividing in culture, and can be applied as a renewable resource from which neurons and neuronal systems may be generated using valproate or analogs.

Treatment of CNS or PNS Disorders

CNS disorders such as neurodegenerative diseases have a major impact on society. For example, approximately 3 to 4 million Americans are afflicted with the chronic neurodegenerative disease known as Alzheimer's disease. Other examples of chronic neurodegenerative diseases include diabetic peripheral neuropathy, multiple sclerosis, amyotrophic lateral sclerosis, Huntington's disease and Parkinson's disease. Not all neurodegenerative diseases are chronic. Some acute neurodegenerative diseases include stroke, schizophrenia, bipolar disorder, unipolar depression, and epilepsy as well as hypoglycemia and trauma resulting in injury of the brain, peripheral nerves or spinal cord. There is a need for improved therapeutic agents and methods for reversing and retarding neuronal damage associated with each of these conditions, or promoting neuronal generation.

A common feature of neurodegenerative disorders and the process of aging in animals is the progressive cell damage of neurons within the central nervous system (CNS) or peripheral nervous system (PNS) leading to loss of neuronal activity and cell death. This loss of activity has been correlated with adverse behavioral symptoms including memory loss and cognitive deficits. Therapeutic agents that have been developed to retard loss of neuronal activity either have toxic side effects or are prevented from reaching their target site because of their inability to cross the blood-brain barrier. The blood-brain barrier is a complex of morphological and enzymatic components that retards the passage of both large and charged small molecules thereby limiting access to cells of the brain. There is thus a need for novel therapeutic agents that are readily transported across the blood-brain barrier as well as for novel methods of treatment of neurodegenerative disorders that directly target the damaged site and are non-toxic.

It is now recognized that neuronal cell density has an important impact on function. In various pathological conditions, loss of cell density has been observed resulting from accelerated neuronal cell death. The pattern of degeneration of neurons typically originates from the nerve terminals and progresses "backward" toward the cell body (retrograde degeneration). In several systems, lesioning of certain brain regions results in compensatory sprouting of axons. This plasticity of neurons is attributed at least in part to the presence of trophic growth factors (Baumgartner et al., J Neurosci 1997;17:6504–6511; Himes et al., Neurosci Res 2001;65:549–564; Linnarson et al., Brain Res Mol Brain Res 2000;75:61–69; and Mamounas et al. J Neurosci 1995; 15:7929–7939.) At present, however, there is no treatment for neurodegenerative disease which effectively prevents, retards, or turns around the progressive neurodegeneration of the brain and cognitive decline associated with the illness.

In animal models and cell cultures, neurotrophic and neuritogenic factors such as nerve growth factor (NGF) and gangliosides, have demonstrated initial therapeutic effects, which indicates that these substances may be of benefit to patients afflicted with Alzheimer's disease. See Frey, W. H., II and T. A. Ala, Progress in Clinical Neuroscience 1:287–303 (1988), and Seiler, Brain Res. 300:33–39 (1984). Potentially, therapeutic agents could be identified that compensate for cell loss by stimulating sprouting of dendrites and axons of remaining cells so as to improve the structural integrity of the damaged region.

Alternatively, treatment of neurological disorders, such as neurodegenerative diseases and neurotrauma, has focused on replacing damaged neural cells with healthy cells. U.S. Pat. No. 5,762,926 to Gage et al., and U.S. Pat. No. 6,395,546 to Zobel et al. hereby incorporated herein by reference, describe neuronal transplantation. Such strategies could be used to replace the injured or depleted neural cells with new neural cells, thus potentially providing treatment of spinal cord injuries and progressive neurodegenerative disorders such as Alzheimer's disease, Parkinson's disease, Huntington's disease, amyotrophic lateral sclerosis and hereditary ataxia as well as to study other diseases, conditions and disorders characterized by loss, damage or dysfunction of neurons including transplantation of neuron cells into individuals to treat individuals suspected of suffering from such diseases, conditions and disorders. Recent studies utilizing human fetal mesencephalic tissue grafts to ameliorate the extrapyramidal manifestations of drug induced and idiopathic Parkinson's disease emphasize the potential of transplanted human CNS tissues for the treatment of human neurodegenerative diseases (Freed, C. A., et al. 1992 New Engl. J. Med. 327:1549–1555; Spencer, D. D. et al. 1992 New Engl. J. Med. 327:1541–1548; and Widner, H., et al. 1992 New Engl. J. Med. 327:1556–1563). However, major obstacles in the field of neuronal transplantation is the inadequacy of donor material, the inability in the prior art of the transplant to fully integrate into the host tissue, and the lack of availability of cells in unlimited amounts from a reliable source for grafting. Since adult neural tissue undergoes minimal division, it does not readily meet these criteria. While in recent years, therapeutic transplantations have been performed using human fetal tissue as the donor substrate, this is a controversial ethical dilemma which is also hampered by critical methodological difficulties. A renewable source of normal human neural cells would be an indispensable tool in clinical studies of neurotrauma and neurodegenerative diseases.

Accordingly, the findings of the present invention can be used for (a) stimulating the differentiation of neurons from adult stem cells in vivo, or (b) providing a source of cells for neural transplantation.

Stimulating neural differentiation in vivo. As described herein, valproate can be used to promote the differentiation of neural stem cells into neurons. Thus, compounds or analogs that are determined to have valproate-like activity may be administered (e.g., to an individual suffering from a CNS disorder) at therapeutically effective doses to enhance neuronal differentiation in vivo. A "therapeutically effective dose" is an amount of the compound that is sufficient to result in enhanced differentiation of neural stem cells into neurons.

Toxicity and therapeutic efficacy of valproate can be determined by standard pharmaceutical procedures, for example in cell culture assays or using experimental animals to determine the LD50 and the ED50. The parameters LD50 and ED50 are well known in the art, and refer to doses of a compound that are lethal to 50% of a population and therapeutically effective in 50% of a population, respectively. The dose ratio between toxic and therapeutic effects is referred to as the therapeutic index and may be expressed as the ratio: LD50/ED50. Compounds that exhibit large therapeutic indices are preferred. While compounds that exhibit toxic side effects may be used. However, in such instances it is particularly preferable to use delivery systems that specifically target such compounds to the site of affected tissue so as to minimize potential damage to other cells, tissues or organs and to reduce side effects.

Data obtained from cell culture assay or animal studies may be used to formulate a range of dosages for use in humans. The dosage of compounds used in therapeutic methods of the present invention preferably lie within a range of circulating concentrations that includes the ED50 concentration with little or no toxicity (e.g., below the LD50 concentration). The particular dosage used in any application may vary within this range, depending upon factors such as the particular dosage form employed, the route of administration utilized, the conditions of the individual (e.g., patient), and so forth.

A therapeutically effective dose may be initially estimated from cell culture assays and formulated in animal models to achieve a circulating concentration range that includes the IC50. The IC50 concentration of a compound is the concentration that achieves a half maximal inhibition of symptoms (e.g., as determined from the cell culture assays). Appropriate dosages for use in a particular individual, for example in human patients, may then be more accurately determined using such information. Alternatively, amounts administered to patients for other purposes, e.g., in the case of buspirone, to treat depression, can be tested for their safety and efficacy in treating CNS disorders characterized by neuronal damage or depletion of.

Pharmaceutical compositions for use in accordance with the present invention may be formulated in conventional manner using one or more physiologically acceptable carriers or excipients. Thus, the compounds and their physiologically acceptable salts and solvates may be formulated for administration by inhalation or insufflation (either through the mouth or the nose) or oral or parenteral administration. For oral administration, the pharmaceutical compositions may take the form of, for example, tablets or capsules prepared by conventional means with pharmaceutically acceptable excipients such as binding agents (e.g., pregelatinized maize starch, polyvinylpyrrolidone or hydroxypropyl methylcellulose); fillers (e.g., lactose, microcrystalline cellulose or calcium hydrogen phosphate); lubricants (e.g., magnesium stearate, talc or silica); disintegrants (e.g., potato starch or sodium starch glycolate); or wetting agents (e.g., sodium lauryl sulphate). The tablets may be coated by methods well known in the art. Liquid preparations for oral administration may take the form of, for example, solutions, syrups or suspensions, or they may be presented as a dry product for constitution with water or other suitable vehicle before use. Such liquid preparations may be prepared by conventional means with pharmaceutically acceptable additives such as suspending agents (e.g., sorbitol syrup, cellulose derivatives or hydrogenated edible fats); emulsifying agents (e.g., lecithin or acacia); non aqueous vehicles (e.g., almond oil, oily esters, ethyl alcohol or fractionated vegetable oils); and preservatives (e.g., methyl or propyl p hydroxybenzoates or sorbic acid). The preparations may also contain buffer salts, flavoring, coloring and sweetening agents as appropriate.

Preparations for oral administration may be suitably formulated to give controlled release of the active compound. For administration by inhalation, the compounds for use according to the present invention are conveniently delivered in the form of an aerosol spray presentation from pressurized packs or a nebuliser, with the use of a suitable propellant, e.g., dichlorodifluoromethane, trichlorofluoromethane, dichlorotetrafluoroethane, carbon dioxide or other suitable gas. In the case of a pressurized aerosol the dosage unit may be determined by providing a valve to deliver a metered amount. Capsules and cartridges of e.g., gelatin for use in an inhaler or insufflator may be formulated containing a powder mix of the compound and a suitable powder base such as lactose or starch.

The compounds may be formulated for parenteral administration by injection, e.g., by bolus injection or continuous infusion. Formulations for injection may be presented in unit dosage form, e.g., in ampoules or in multi dose containers, with an added preservative. The compositions may take such forms as suspensions, solutions or emulsions in oily or aqueous vehicles, and may contain formulatory agents such as suspending, stabilizing and/or dispersing agents. Alternatively, the active ingredient may be in powder form for constitution with a suitable vehicle, e.g., sterile pyrogen free water, before use. The compounds may also be formulated in rectal compositions such as suppositories or retention enemas, e.g., containing conventional suppository bases such as cocoa butter or other glycerides.

In addition to the formulations described previously, the compounds may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example as an emulsion in an acceptable oil) or ion exchange resins, or as sparingly soluble derivatives, for example, as a sparingly soluble salt. The compositions may, if desired, be presented in a pack or dispenser device that may contain one or more unit dosage forms containing the active ingredient. The pack may for example comprise metal or plastic foil, such as a blister pack. The pack or dispenser device may be accompanied by instructions for or administration.

Neural transplantation. The differentiated neurons or differentiating neural stem cells produced by the method of the present invention may be used to treat individuals suffering from injuries, diseases, conditions or disorders characterized by the loss, damage or dysfunction of endogenous cells. Transplantation of the differentiated neurons or differentiating neural stem cells neurons may be used to treat individuals suffering from stroke, spinal injury or other injuries, conditions or disorders associated with neuron damage or death. CNS diseases and disorders which may be treated include any disease of the CNS which is characterized by the loss, damage or dysfunction of endogenous cells, the symptoms of which may be reversed or reduced in severity by providing neurons that can replace such cells and produce products needed for proper function or needed to counteract the presence of compounds that are not normally present or present at abnormal levels. The present invention is useful for the treatment of progressive neurodegenerative disorders such as Alzheimer's disease, Parkinson's disease, Huntington's disease, amyotrophic lateral sclerosis and hereditary ataxia, as well as neurological conditions such as strokes and nerve injuries. The multipotent neural stem cell progeny can be continuously passaged and proliferation reinitiated in the presence of valproate to result in an unlimited supply of neural cells for neurotransplantation and other purposes.

In a further embodiment, the neural stem cells obtained using the method of the present invention can be manipulated to express desired gene products. The proliferating neural cells can be transfected with exogenous DNA to produce genetically modified neural stem cell progeny. Alternatively, the neural stem cells can be transfected prior to differentiation according to the invention. The genetic modification can be for the production of biologically useful proteins such as growth factor products, growth factor receptors, neurotransmitters, neurotransmitter receptors, neuropeptides and neurotransmitter synthesizing genes.

Neurons may be implanted into the brain, spinal cord, or at or near the site of nerve damage from disease or injury. Neurons of the invention are implanted at the site of the nerve cell injury, i.e., in proximity to the injured cell or cells at a location where the implanted cells can replace nerve function and/or reconnect nerves of the individual to remedy or otherwise ameliorate the injury or disorder.

The transplanting of cultured cells of the invention into the brain of an animal, including a human, is a relatively simple process. A tube of appropriate diameter is inserted to the desired region of the brain, e.g., the striata, and a suspension of cells in a physiologically acceptable carrier is allowed to flow through the tube into the brain at a controlled rate, to the desired location. A physiologically acceptable carrier can be any sort of solution having non-toxic, non-injurious components for either the cells or the tissue at the site of transplant. Typically, a physiologically acceptable carrier will include a solution of salts compatible with live cells and tissue having pH, osmolarity and chemical composition ranges known in the art, for example, Hank's buffer.

Presently, one main technique or a variation thereof is used for transplanting neural tissue. See e.g., Kordower, J. H. et al. (1995) N. Engl. J Med. 332(17):1118–1124; Freeman, T. et al. (1995) Annals Neurol. 38(3):379–388; Widner, H. et al. (1992) N. Engl. J. Med. 327(22):1556–1563. This technique employs a cell or tissue delivery device which includes a stereotaxic needle with a blunt end and a tip diameter from about 0.9 to about 1.5 mm. The cells or tissue to be transplanted are loaded into this needle, the needle is advanced toward the transplant site, and the cells or tissue are released from the needle at the site. Using this needle, multiple grafts can be placed along a straight path. However, if one wishes to graft at a site which is not along this path, the needle must be removed and reinserted along a new path. Reinsertion of this needle causes additional trauma to the tissue in the path of the needle. Typically, it is desirable to make multiple grafts along different paths. In such a case, the needle is generally removed and reinserted into the subject from about six to about eight times per side of the brain, increasing trauma to the brain tissues with each new penetration.

In addition to the simple injection needles described above, other instruments have been described for transplantation of tissue into the brain. See U.S. Pat. Nos. 5,006,122 and 5,004,457. U.S. Pat. No. 5,006,122 discloses a brain tissue transplantation method utilizing a cannula within a cannula assembly. The first cannula is a large bore cannula which is fixed to a stereotaxic holding apparatus and which is advanced into the brain to the transplant site. The second cannula, which carries donor tissue and a stylet which is used to expel the tissue from the second cannula, is guided within the lumen of the first cannula to the transplant site. The tissue is then transplanted into the brain by withdrawing the first and second cannulas while the stylet within the second cannula is maintained in a fixed position. The stylet is later removed, leaving only the transplanted tissue in the recipient.

In addition, U.S. Pat. No. 5,792,110 describes a system for delivering therapeutic agents, including cells, to a selected site in a subject, including the brain, to a predetermined depth using a delivery cannula for delivering the therapeutic agent to the subject. The guide cannula has an axial bore extending therethrough with an open proximal end and an opening at a distal portion thereof. The delivery cannula has an axial bore extending therethrough, a flexible distal end portion, and an outer diameter which is less than the inner diameter of the guide cannula.

In summary, the capacity to efficiently differentiate neurons as opposed to protect mature neurons from injury or degeneration is important both for the treatment of neurodegenerative diseases and in vitro studies of cells to be used in transplantation, or to be used for research and drug screening processes.

EXAMPLES

Examples of practicing the invention are provided, and are understood to be exemplary only, and do not limit the scope of the invention or the appended claims. A person of ordinary skill in the art will appreciate that the invention can be practiced in many forms according to the claims and disclosures here.

Example 1

Differentiation of Neural Stem Cells into Neurons Using Valproate

This Example describes the differentiation neural stem cells obtained from rat. Stem cell differentiation was initiated by removal of bFGF, and the amount of neurons obtained after exposure to valproate estimated by staining with an anti-β-tubulin antibody, using either untreated cells or cells exposed to BNDF as controls.

Methods

Drugs. A valproate solution was prepared by dissolving valproate (Sigma) in NaCl 0.9%. Aliquots were made and frozen at −80° C. Before treatment, one aliquot was thawed and kept for 1 week at 4° C.

Isolation of cortical and striatal stem cells. Timed pregnant Sprague Dawley rats were obtained from Taconic at embryonic age E14–E15 were sacrificed by inhalation of excess carbon dioxide. The abdomen of the rat was cleaned with 70% ethanol and the uterus was removed quickly and aseptically on the bench top. The uterus was placed in ice cold HBSS (GIBCO Cat. #20012-027) in a 10 cm petridish. After rinsing the uterus in PBS, embryos were removed from the uterus, rinsed in HBSS and collected in cold HBSS (buffered with HEPES and sodium bicarbonate) in a 10 cm petridish and placed on ice.

The cortex and striatum (lateral ganglionic eminence) was dissected under a microscope and collected in a 15 ml tube of HBSS, on ice. Removal of meninges is not possible at this age, and no attempt was made to do so. If the dissected tissue was in large enough chunks and settle to the bottom of the tube, no centrifugation was performed. Alternatively, the tube was centrifuged at 1000 rpm for 5 minutes to pellet the tissue. Following centrifugation, the 15 ml tube containing the tissue was sprayed with 70% ethanol and taken into the sterile hood.

The HBSS was aspirated and replaced with 2 ml of DMEM/F12. Cells were dissociated by trituration, followed by addition of 5 ml of DMEM/F12 and a second round of trituration. There remained smaller chunks of tissue in the tube after dissociation, along with 'sheets' of meninges.

The tubes were placed standing 5–10 minutes in the hood to allow larger particles and meninges to settle. After the meninges settled, a cell count was made. 10 μl of the cell suspension is diluted with trypan and counted in a hemocytometer. Cells were counted in the four outer chambers with the larger squares, and cell count calculated assuming that the volume enclosed in each of the chambers was 0.1 ml.

Preparation of culture medium and tissue culture dishes. Prior to plating of isolated cells, 10 cm culture dishes (Falcon) were incubated at 37° C. overnight with 5 ml of 1.5 mg/ml poly-ornithine (Sigma Cat #P-3655) dissolved in water. Following overnight incubation, the dishes were washed twice with ddH2O, coated with 5 ml of 1 mg/ml fibronectin (Invitrogen Cat #33010-018) in PBS, and incubated overnight. Following incubation, the culture dishes were washed once with PBS, filled with PBS, and stored in the incubator until use. The coated dishes should not be stored at 37° C. for more than 5 days.

Growth medium was prepared according to the following:

| DMEM/F12 medium: | |
|---|---|
| 1 pack | DMEM-F12 powder (GIBCO Cat. # 12500-039) |
| 1.55 g | D-(+)-Glucose (SIGMA Cat. # G-8270) |
| 1.69 g | NaHCO3 (SIGMA Cat. # S-5761) |
| 73 mg | L-Glutamine (SIGMA Cat. # G-5763) or 10 ml of GlutaMAX (GIBCO) |
| 800 ml | ddH2O |

The above-listed reagents were mixed using a magnetic stir bar until completely dissolved. The pH was to 7.2 by the addition of 1N HCl as assessed using a pH meter. The total volume was adjusted to 990 ml and filter-sterilized. 10 ml were taken for preparation and dilution of the N2 supplement (see below). 10 ml of 100×Penicillin-Streptomycin (GIBCO Cat. #15070-063) was added to the medium.

| DMEM/F12/N2: | |
|---|---|
| The following reagents were added to about 10 ml of the above medium: | |
| 100 μl | 1M Putrescine (SIGMA Cat. # P-5780) |
| 60 μl | 0.5 mM Sodium selenite (SIGMA Cat. # S-5261) |
| 200 μl | 0.1 mM Progesterone dissolved in EtOH (SIGMA Cat. # P-8783) |
| 100 μg | Human apo-transferrin (SIGMA Cat. # T-2036) |
| 10 μl | 100 x Penicillin-Streptomycin (GIBCO Cat. # 15070-063) |

All the components were dissolved and filter-sterilized. The 10 ml was then added back to the DMEM/F12 medium.

| Added to the medium immediately prior to use: | |
|---|---|
| Insulin | (INTERGEN Cat. # 4501-01) at 25 mg/L |
| 10 ng/ml | recombinant human basic fibroblast growth factor (bFGF, R&D Systems) |

Following addition of N2, the growth medium was sterile filtered and stored at 4° C. protected from light. This medium was not used after 2 weeks of storage.

Plating, expansion and passaging of cortical and striatal stem cells. A generous amount of the triturated cell suspension was left in the original 15 ml tube to avoid fibroblast contamination in cultures. About 4–5 ml of the 6 ml of cells suspension was used for plating. Cells were plated at a concentration of $1.3 \times 10^3$ cells to to $3.0 \times 10^3$ per $cm^2$ in 100 mm dish. This culture is designated P0 (passage 0).

Following plating cells were expanded for about 3–4 days (Passage 1, P1). Cells were treated daily with 10 ng/ml bFGF. The cultures were never permitted to reach more than 70% confluency. Cultures were then passaged as follows: 10 ml of HBSS without $Ca^{2+}$ and $Mg^{2+}$ was added to each 100 mm dish and the cells incubated at 37° C. for 5–15 minutes, or until sufficient numbers of the stem cells were rounded up. It is not expected that all cells in the culture will round up as there are several cell types in the culture at P0. The pH of the HBSS should be neutral at all times during this incubation. Cells were then removed from the dish by pipetting with a 5 ml pipette, and collected in a 15 or 50 ml conical tube, and centrifuged at 1000 g for 5 minutes. Cells were gently re-suspended in medium, counted, and plated at a density of $1 \times 10^6$ cells in 10 cm dishes and expanded for about 2 days in bFGF (Passage 1, P1). At that time the cells were passaged as described and plated onto pre-coated poly-L-ornithine/fibronectin vessels at concentrations indicated below for each experiment. Cells were treated with bFGF for 2 additional days. Before each treatment the bFGF was removed from the cells by washing twice with DMEM/F 12 to induce cell differentiation. For neurite outgrowth experiments, cells were seeded at $5 \times 10^3$ cells/well in 24-well plates and treated immediately.

Preparation of the neuronal conditioned medium (NCM). NCM was obtained from a conditioned medium of cultures from primary rat cortical neurons. Briefly, brain hemispheres from E19 rats were removed and placed in HBSS as described above. Cortexes were isolated and incubated with papain and DNAseI for 10 min at 37° C. Tissue was dissociated by trituration 15 times using a 1 ml pipetteman. Cells were seeded at $3 \times 10^6$ cells in 100 mm Petri dishes pre-coated with poly-L-ornithine/fibronectin (1 mg/ml) and grown in MEM with B27 medium for 3 weeks. Fresh medium was added and collected after 3 days, followed by centrifugation, and stored at 4° C. prior to use.

Expansion and differentiation of striatal human stem cells. Human stem cells (line 161) were provided from ReNeuron Inc. (U.K.). Striatum was obtained after 6 to 12 weeks of gestation from routine legal abortion. Cell line (line 161) was provided by ReNeuron at passage 16. The stem cells were expanded in untreated 25 $cm^2$ tissue culture flasks (Nunc, USA) in the presence of 20 ng/ml and 10 ng/ml of human recombinant EGF and bFGF respectively, in NSA basal serum-free medium (Euroclone, U.K). Fresh medium and growth factors were added every 3 days. In these conditions stem cells were growing as floating neurospheres. After 4 weeks, the neurospheres were harvested, treated with a mild papain treatment in HBSS and dissociated into a single cell suspension. Cells were counted and viability was estimated by trypan blue exclusion method. Cells were differentiated by growth factors removal. The cells were plated in NSA medium at 20,000 cells/well on LabTek permanox culture slides of 8 wells precoated with laminin (1 μg/ml). Cells were treated with valproate and BDNF for 9 days at 37° C. and a saturated humidified atmosphere of 5% $CO_2$, 1% $O_2$ and 94% $N_2$. Fresh medium and re-treatment with factors was performed every 3 days.

Drug treatment. For immunofluorescence and Western analysis, cells were treated daily with either 0.5 mM of valproate (Sigma), 10 ng/ml of BDNF (R & D Systems), 20 ng/ml of NT-3 (R & D Systems), 1 nM 9cis retinoic acid (Sigma) or a dilution of NCM for 6 or 7 days. In some experiments valproate was also added with NCM and/or 9cis RA for 7 days. For human stem cell experiments, valproate (0.5 mM) or BDNF (25 ng/ml) was added for 9 days. For neurite outgrowth experiments, cells were treated for 1 day with 0.5 mM valproate or 50 ng/ml of BDNF. Where applicable, medium was changed every 2 days. After about 5–10 days, preferably on day 6 (i.e., after 6 days of drug exposure) the cells were fixed with a 4% solution of para-formaldehyde (PFA) in PBS, prepared as follows:

PFA:
4 g of paraformaldyde.
4.1 g of sucrose
80 ml of PBS

The solution was heated to approximately 70–80° C. for about 2–3 hours under a chemical hood while stirring to medium speed. Solution was not allowed to boil. Once the solution became clear, the pH was measured using pH paper and adjusted with sodium hydroxide to about. 7.2. The volume was adjusted to 100 ml and filtered. Solutions older than 1 week should not be used.

For fixing, the medium was aspirated from the cell culture dishes, and cells were exposed to 0.5 ml of PFA for 15–20 minutes at room temperature. Cells were then washed twice with PBS for 15 minutes each.

Western blotting. Cells were plated at $1 \times 10^6$ cells/100 mm dish in poly-1-ornithine-coated 10 cm dishes and treated as described supra. Denatured proteins were separated on 8% polyacrylamide Tris-Glycine gels (Novex) and transferred to nitrocellulose membranes (BioRad). Membranes were probed with antibodies against rabbit anti-GAD 65/67 (Sigma) at 1:10,000 and HRP-conjugated anti-rabbit (Jackson Immunolabs) at 1:10,000 respective dilutions.

Antigen-antibody complexes were visualized using a SuperSignal West Pico Chemiluminescent Kit (Pierce).

Immunofluorescent staining and visualization. Cells were plated at 20,000 cells/well in poly-L-ornithine/fibronectin (1 mg/ml) coated 24-well plates. After fixation, the PBS was aspirated from the fixed cells and the cells were treated with blocking solution (10% normal goat serum-NGS-Jackson Labs), 0.3% Triton-Sigma, in PBS) to saturate non-specific sites and permeabilize the cells. Following blocking, cells were incubated with the following designated primary antibodies diluted in PBS with 5% NGS for 1 hour at room temperatuare: mouse monoclonal anti-MAP-2 (Sigma): 1/250 dilution; mouse monoclonal anti-β tubulin III (Covance): 1/2000 dilution; mouse monoclonal anti-β tubulin III (Sigma); rabbit anti-monoclonal glial fibrillary acidic protein (GFAP-Dako): 1/500 dilution; and rabbit anti-Gamma Aminobutyric Acid (GABA; Sigma): 1/2000 dilution.

After the 1 hour incubation, cells incubated with anti-MAP-2, anti-β tubulin III, and anti-GFAP were washed three times for 5 min each with PBS followed by incubation of a goat anti-mouse secondary antibody conjugated with stains Cy2 and Cy3 (Jackson Labs) for 1 hr at RT (dilution 1/1000 as with the primary antibodies). Following three 5 minute washes with PBS, cells were incubated with 0.2 ug/ml of nuclear stain bis-benzamide for 20 minutes (Sigma) at RT. Cells were then washed 3 times with ultra-pure water and glass coverslips were mounted on them using AquaPoly-mount (Polysciences Inc., Warrenton, USA) The mount was allowed to dry and the dishes were stored at 4° C.

For visualization of staining, the mounted cells were viewed under an Olympus inverted fluorescent microscope IX70 with a Xenon lamp using the appropriate ultra violet filters.

For GABA staining, a biotin-streptavidin amplification was used. After primary antibody had been removed, neural stem cells were incubated with biotin-conjugated anti-rabbit (Vector) at 1:300 for 30 minutes. Secondary antibody was removed by washing three times in PBS. NSCs were incubated with either HRP-conjugated streptavidin-biotin complex (ABC kit, Vector) or with Cy2-conjugated streptavidin (Jackson ImmunoResearch Labs) at 1:300 for 30 minutes followed by 3 washes of PBS. Detection of GABA immunocytochemistry was performed using a DAB detection kit (Vector) according to manufacturer's instructions.

For analysis of neurite outgrowth, digital images were taken with an ArrayScan HCS System (Cellomics, Pa.) of 100 cells/well treated with valproate (0.5 mM) and BDNF (50 ng/ml) for 1 day. All cells were identified by labeling the nuclei with Hoechst Dye. The neurites and cell bodies of the neurons were identified by indirect β tubulin-III immunofluorescence. Neurite outgrowth index is defined as the percentage of cells whose neurites total more than 20 μm in length, and is calculated using Cellomics' Neurite Outgrowth application.

For counting, three to five different fields of interest at magnification 10× or 20× were chosen randomly. For immunofluorescence, 3 different black and white pictures were taken by field of interest with a digital camera CoolSnap Fx (Princeton) corresponding to the exposure of Cy2, Cy3 and Hoechst fluorescence. Black & white pictures for each channel were merged and assigned with a sudden color by using IPLab (Scanalytics). The number of neurons, astrocytes and GABAergic cells were estimated by counting the cells immunopositive respectively for β-tubulin III, GFAP and GABA. The percentage of neurons, astrocytes and GABAergic cells was determined by comparing the number of cells immunopositive for β-tubulin III, GFAP and GABA to the number of bis-benzamide stained nuclei (i.e., total cell number). Each counting are from 2–3 sister wells and standard deviations represent variation of the mean from 2–3 wells.

Results

Figure 1B:
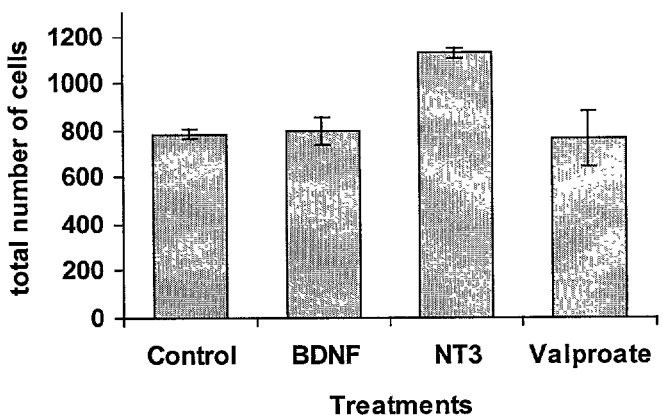
FIG. 1B. This figure shows that valproate does not inhibit neural stem cell proliferation. Results represent the total number of cells from the same field represented in FIG. 1A. The total number of cells was similar to that in control cultures. The total number of cells was estimated by visualizing cell nuclei with bis-benzimide.
Figure 1C:
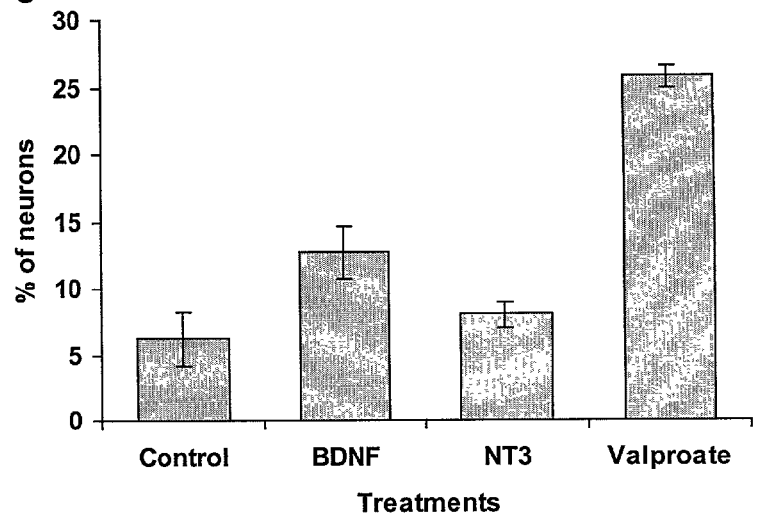
FIG. 1C. This figure demonstrates that valproate increases neuronal differentiation more efficiently than neurotrophins or growth factors. Graph shows the percentage of neurons vs. the total number of cell per field.
Figure 9:
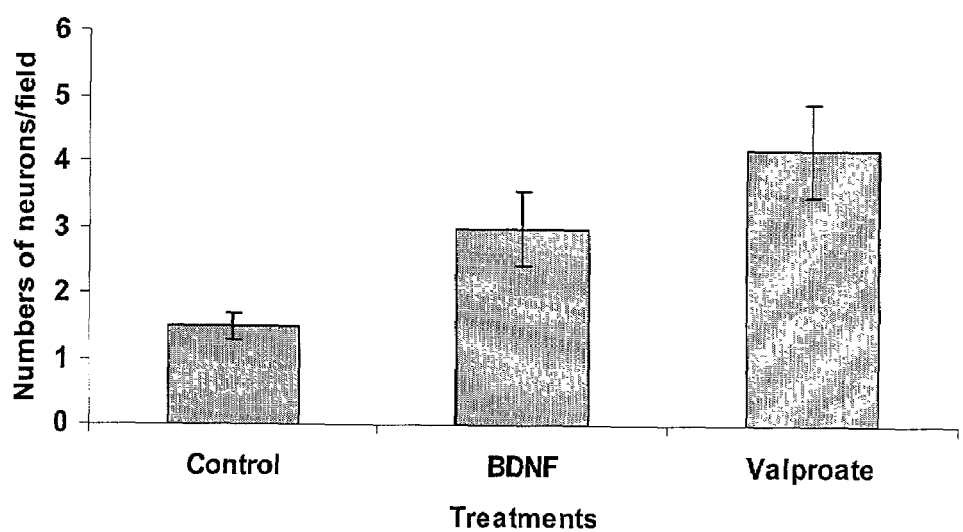
FIGS. 9A–B shows that valproate increases neuronal differentiation in human stem cell culture without inhibiting cell proliferation. Human stem cells from striatum were treated with valproate or BDNF for 9 days. (A) represents the number of β tubulin III neurons per field and (B) the total number of cells per field. Counting were performed on cultures observed at high magnification (objective×40). The total number of cells was estimated by visualizing cell nuclei with bis-benzimide.
Figure 9:
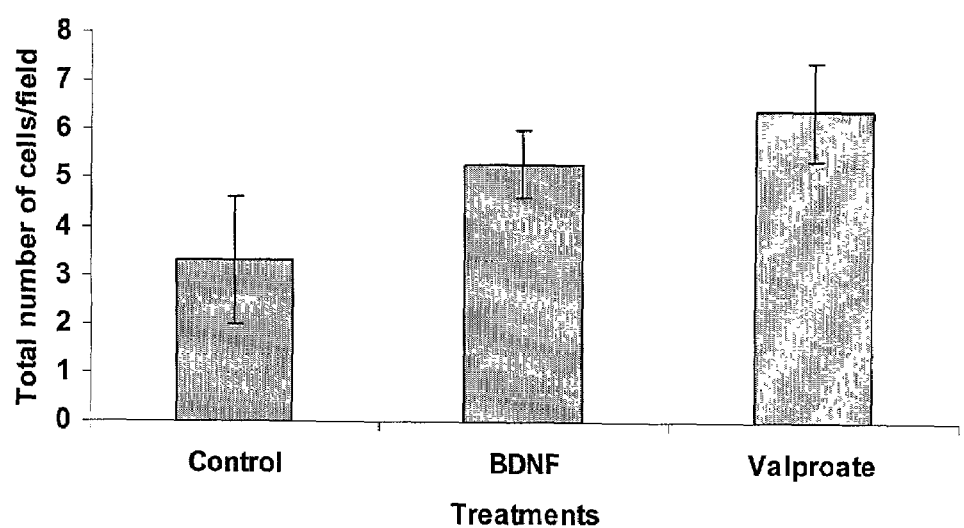

Valproate promotes neurogenesis of rat cortical and striatal stem cells. Valproate increases the percentage of β-tubulin III expressing neurons, originating from cortical neural stem cells, by almost 5 fold over the control (FIG. 1C). This effect and the ability of valproate to increase the number of neurons (FIG. 1A and FIG. 2A) occurred without valproate affecting the total cell number (FIG. 1B). Neurotrophic factors have been reported to increase neuronal differentiation in rat forebrain stem cells. In our conditions only BDNF increased the percentage of β-tubulin-III expressing cells over control but was less effective than valproate. NT-3 didn't have any effect on rat stem cell differentiation into neurons. In valproate cultures, 25.8+0.8% (mean+SD) neurons were obtained vs. 12.7+2% neurons in BDNF culture, 8+1% neurons in NT-3 culture, and 6.2+1.8% neurons in untreated controls. Valproate also increased the percentage and number of neurons in rat stem cells from ventral forebrain i.e. the lateral ganglionic eminence (LGE) and human stem cells from the striatum (data not shown). Human striatal stem cells (obtained from ReNeuron Ltd, Surrey, UK) demonstrated 70% differentiation when treated with 0.5 mM valproate compared with the untreated control, which demonstrated 40% neuronal differentiation (FIG. 9). Similar to rat cortical stem cells, human striatal stem cells also demonstrated enhanced differentiation into neurons with valproate compared with BDNF, which resulted in 58% neuronal differentiation.

Figure 2A:
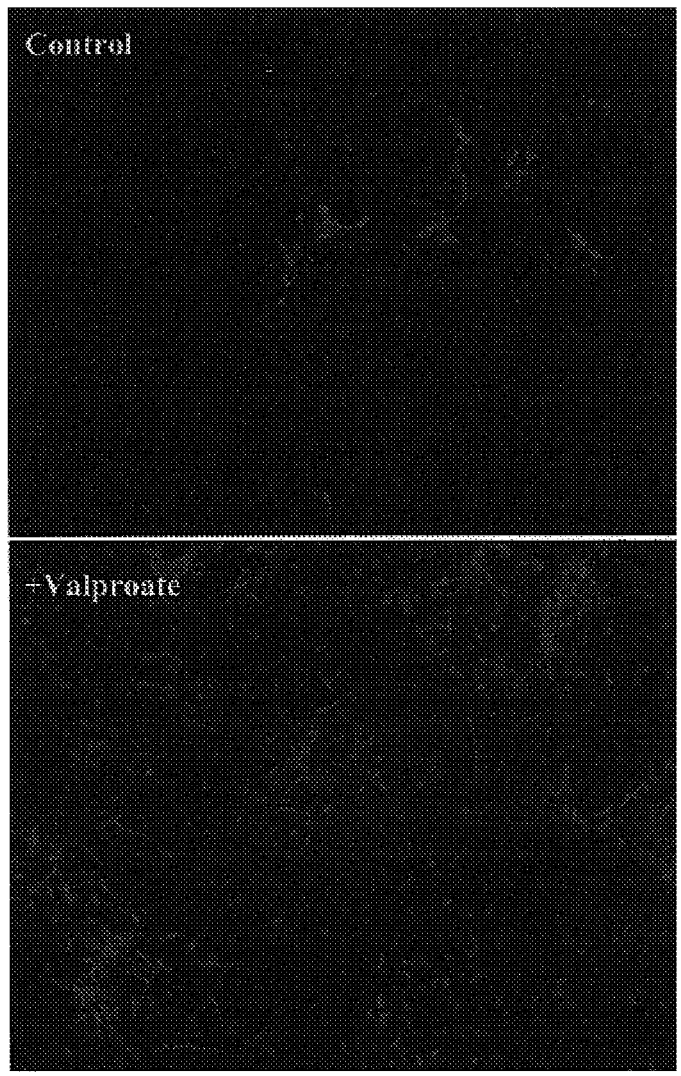
FIGS. 2A–B show differentiated neurons in control cultures compared with valproate-treated cultures. Pictures show one representative 10× objective magnification field from both control and valproate-treated cultures as indicated. Red indicates β tubulin-III positive neurons, and blue, Hoescht-stained nuclei.
Figure 2B:
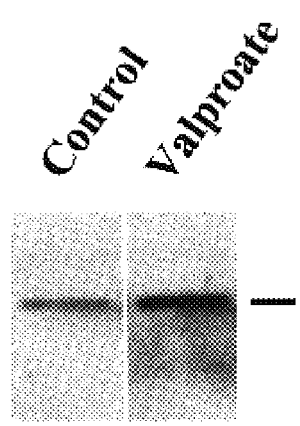

During pregnancy and in other cell culture models, valproate has been reported to affect cellular maturation by inhibiting cell proliferation at the G1 phase. In our conditions, valproate is working with a different mechanism of action since the total number of cells is comparable to control (FIG. 1B and FIG. 2A). The increase of β-tubulin III expression by valproate was confirmed by Western blot already after 1 day of treatment (FIG. 2B).

Figure 3:
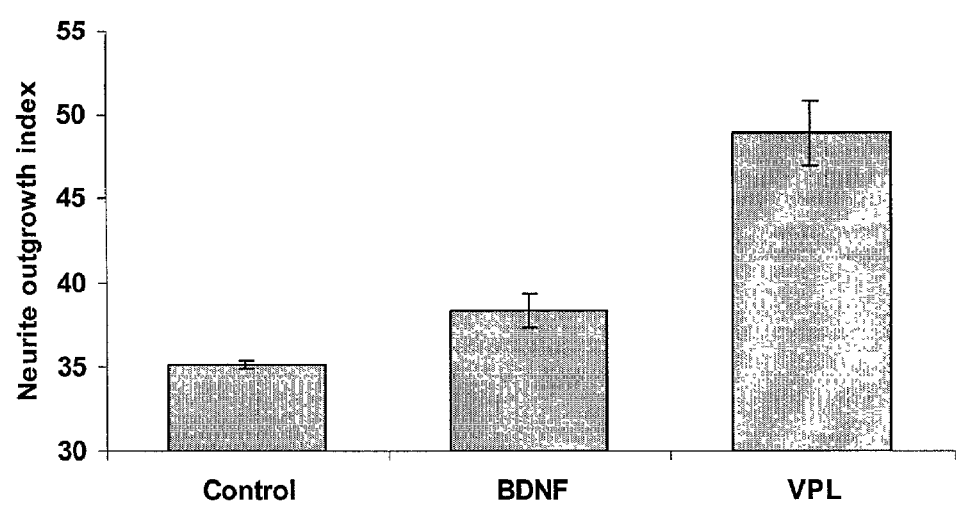
FIG. 3 demonstrates that valproate increases the neurite outgrowth of differentiating neural stem cells. Rat cortical stem cells were treated with valproate or BDNF for one day. Neurite outgrowth represents the percentage of cells whose neurites total more than 20 µm in length.

Valproate promotes neurite outgrowth of neurons derived from rat cortical stem cells. Valproate affects also the morphology of neurons derived from rat cortical stem cells. Cells treated with valproate for 6 days were found to be growing in clusters and had longer process than cells in control (FIG. 2A) or BDNF (not shown) conditions. To estimate the neurite outgrowth index per cells we grew rat cortical stem cells at low density for 1 day with valproate or BDNF. Valproate increases the neurite index when compared to control or BDNF, a neurotrophic factors known to increase neurite outgrowth in neurons from different brain regions. In cultures treated with valproate for 1 day, neurite index was 49+1.9 vs. 35.1+0.3 in control cultures and 38.3+1 in BDNF cultures (FIG. 3).

Figure 4A:
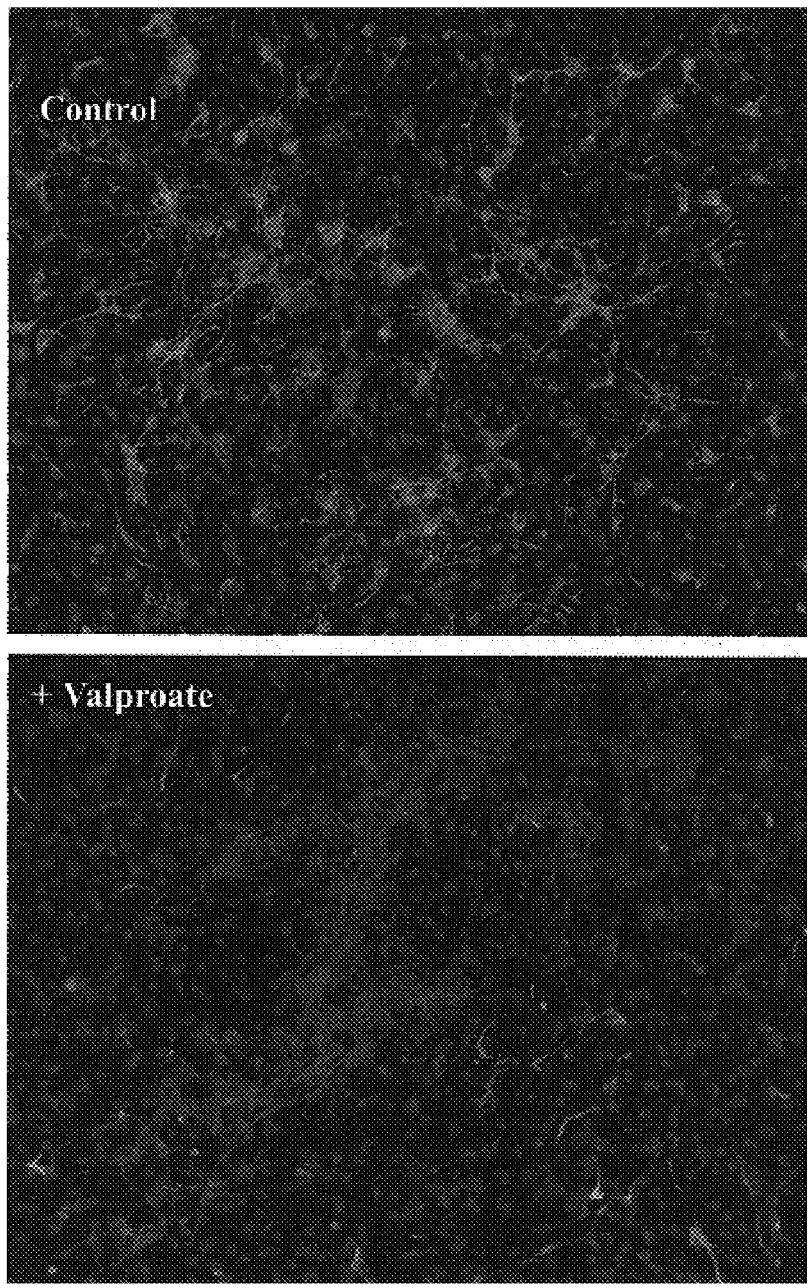
FIGS. 4A–B show that expression of glial acidic fibrillary protein (GFAP), a specific marker for astrocytes (green), was dramatically inhibited in valproate-treated cultures compared to control cultures. Cultures were treated with valproate or vehicle for 6 days. (A) Pictures show immunofluorescence of one representative 10× magnification field from control and valproate-treated cultures as indicated. Red indicates β tubulin-III positive neurons, green GFAP positive astrocytes and blue, Hoescht-stained nuclei. (B) Graphs represent the number of GFAP positive astrocytes per field (top) and the the total number of cells per field (lower) in valproate-treated cultures compared to controls.
Figure 4B:
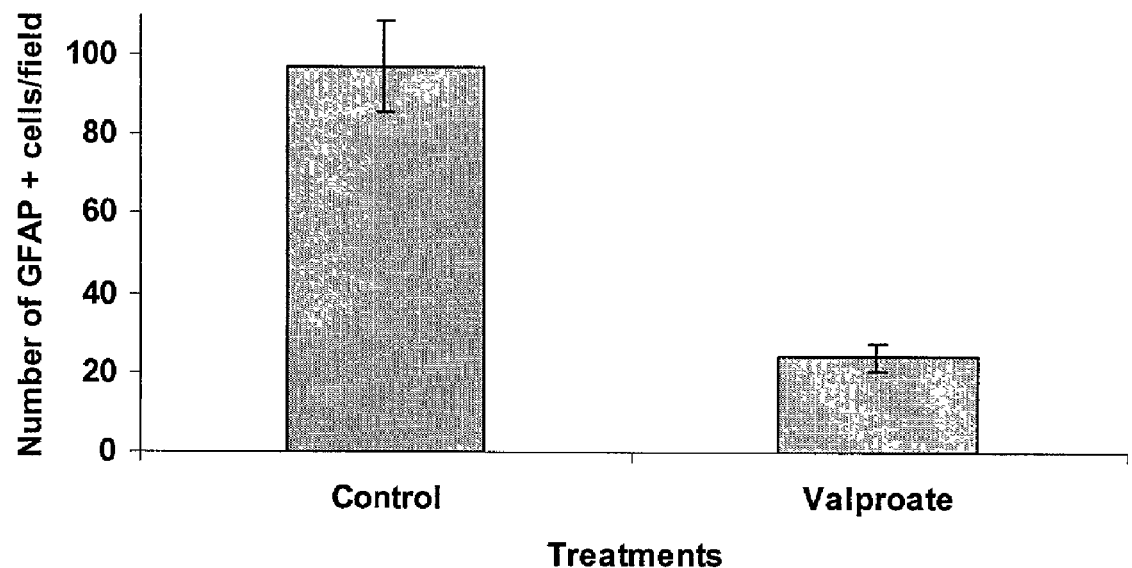
Figure 4B:
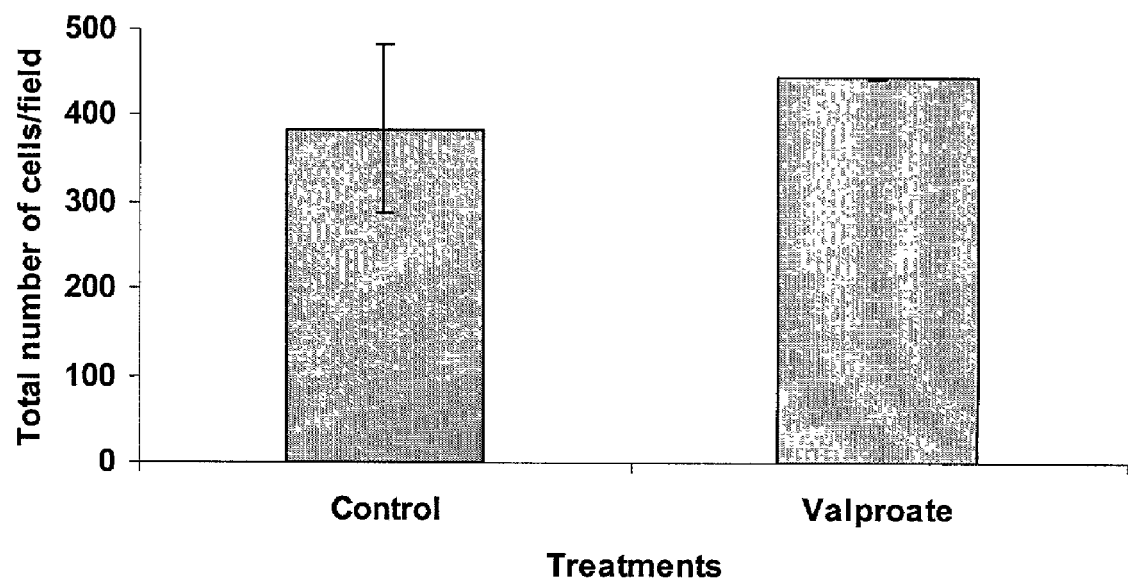

Valproate inhibits the differentiation of rat cortical stem cells into astrocytes. In cultures treated with 6 days with valproate, the expression of glial acidic fibrillary protein (GFAP), a specific marker for astrocytes, was dramatically inhibited compared to control (FIGS. 4A and B) while the expression of β-tubulin III was increased (FIG. 1A and FIG. 2A). This inhibitory effect on the glial differentiation pathway is not the result of a change in cell proliferation since the overall cell densities in control vs. valproate treated cells were similar (FIG. 1B and FIG. 4B).

Taken together, these results suggest that valproate is likely to promote directly the cell commitment to a neuronal cell-type at the expense of astrocyte differentiation.

Figure 5:
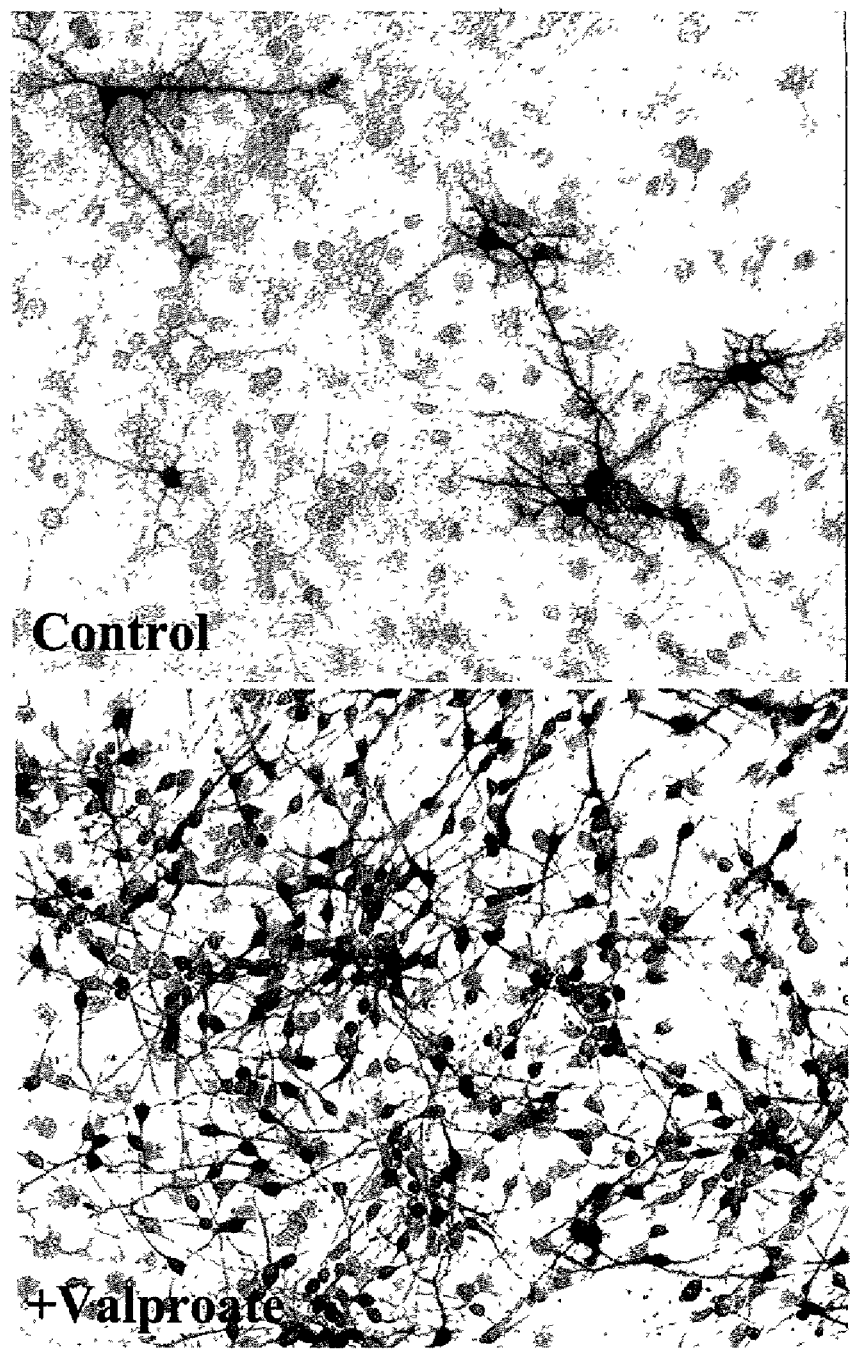
FIG. 5 demonstrates the increase in the number of GABA-positive neurons that differentiated in response to treatment with valproate. Cultures were treated with valproate (+valproate) or vehicle (control) for 6 days. Pictures represent the immunocytochemistry staining for GABA at 10× magnification field.
Figure 6:
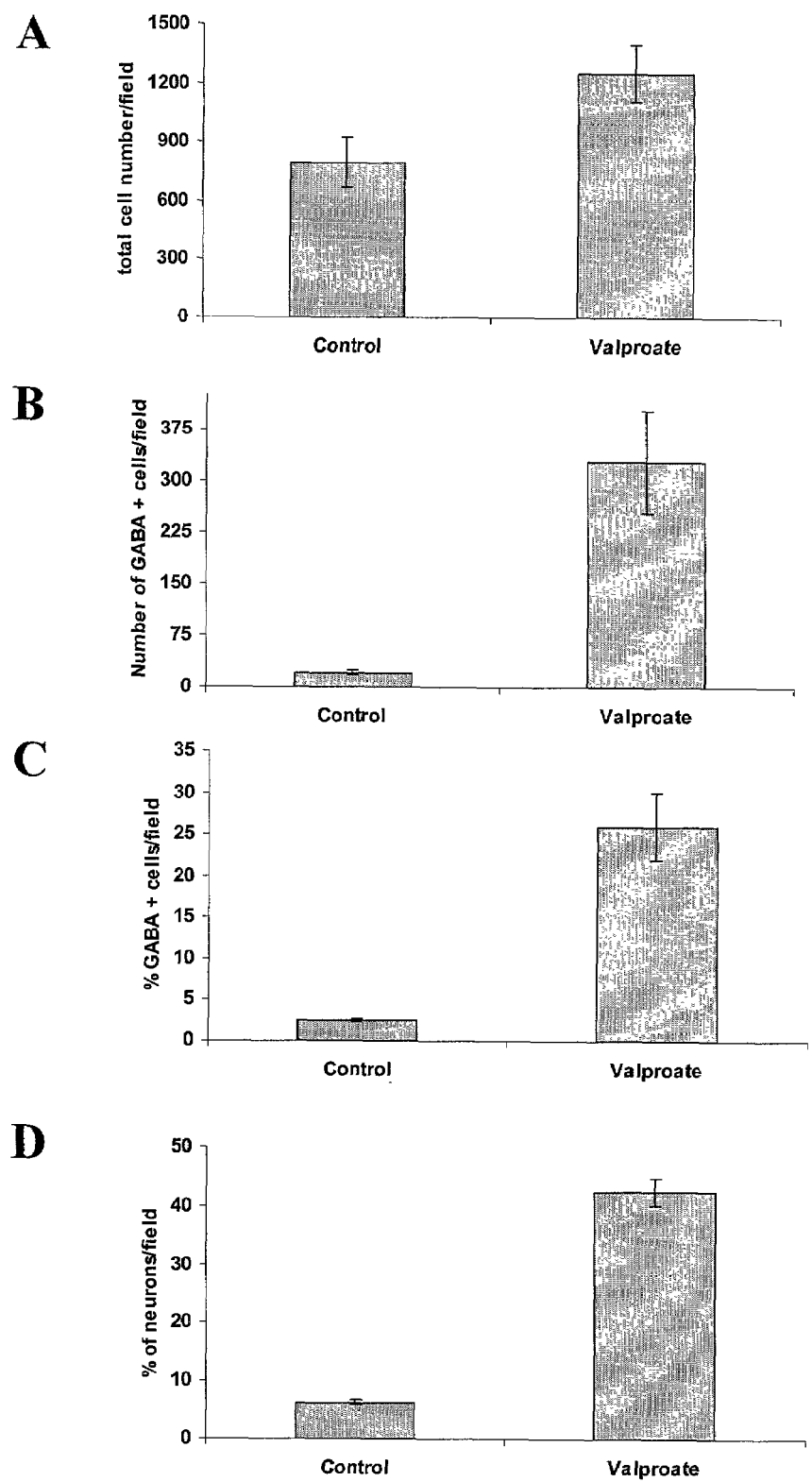
FIGS. 6A–D show that valproate increases the neuronal differentiation of rat cortical stem cells into GABAergic neurons. Cells were treated as described in FIG. 5. The number of GABA immunopositive cells was estimated by bright field while the total cells estimated by phase contrast. (A) represent the total cell number per field, (B) the number of GABA positive cells per field, (C) the percentage of GABA positive cells vs the total cell number per field and (D) the percentage of β tubulin III neurons per field.
Figure 7:
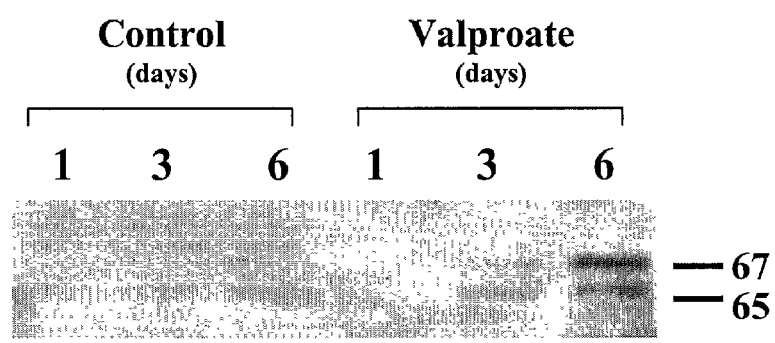
FIG. 7 shows that expression of glutamate decarboxylase (GAD), the synthesizing enzyme for GABA and a definite marker of GABAergic neurons, was stimulated in valproate-treated rat cortical stem cell cultures compared to control cultures. Cells were treated with valproate for 1, 3 or 6 days. Western blots show 2 immunoreactive bands that migrated to 65 and 67 kD, corresponding to GAD isoforms 65 and 67. Note that valproate increases GAD expression after 3 and 6 days of treatment compared to untreated controls.

Valproate increases the differentiation of rat cortical stem cells into GABA expressing cells. Valproate is known to act as an anti-convulsant by increasing the level of GABA (gamma aminobutyric acid) in the brain. Although valproate has been shown to reduce the degradation of GABA by inhibiting GABA transaminase, little is known about its mechanism of action on the GABAergic system. To investigate the effect of valproate on the differentiation of GABAergic neurons, rat cortical stem cells have been grown and treated with valproate as described previously. After 6 days of treatment with valproate, cells have been fixed and processed for GABA immunocytochemistry or immunofluorescence. In this representative experiment, the cultures of stem cells treated with valproate showed a dramatic increase in the number (FIGS. 5 and 6B) and percentage (FIG. 5C) of cells immuno-positive for GABA compared to the control. The same results were obtained when GABA staining was detected by immunofluorescence (data not shown). Western blots were performed on total cell extracts from rat cortical stem cultures treated with 0.5 mM of valproate for 1, 3 and 6 days to detect the expression of the glutamate decarboxylase (GAD), the GABA synthesizing enzyme. Anti-GAD immunoblots revealed two bands migrating at 65 and 67 kD specific for GAD (FIG. 7). No expression of GAD was detectable after 1 day of a vehicle or valproate treatment. GAD expression was increased with valproate after 3 and 6 days of treatment. This result confirms the inductive effect of valproate on the production of GABAergic neurons from rat stem cell. This result is particularly interesting in regard to neurodegenerative disorders that result from loss of GABAergic neurons and which may require grafting of specific neuronal subtypes. Since valproate increases dramatically the differentiation into GABAergic neurons these could be used to replace GABAergic neurons in Huntington's disease. Alternatively, valproate itself could be used for the treatment of Huntington's disease to stimulate the production of de novo GABAergic neurons from adult stem cells or neural progenitors in the brain or other neurodegenerative diseases such as Alzheimer's disease in which GABA neurons are lost or atrophied.

Figure 8:
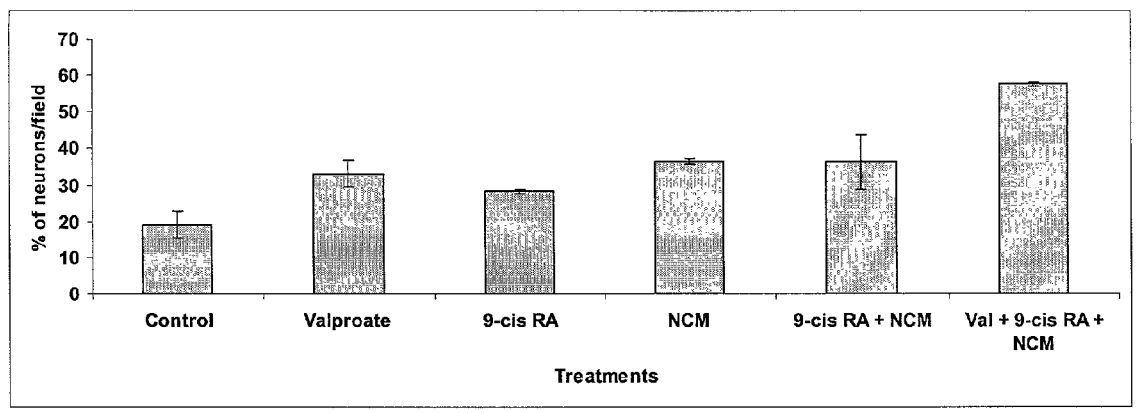
FIG. 8 shows that valproate potentiates the stimulating effect of 9-cis retinoic acid and neuronal conditioned medium on neuronal differentiation in rat cortical stem cells. Rat cortical stem cells were treated for 7 days with either valproate, 9-cis retinoic acid (RA), or neuronal conditioned medium (NCM) alone or together as indicated.

Valproate potentiates the effect of NCM and 9-cis RA on neuronal differentiation. To increase the differentiation in vitro of neurons from rat stem cells, valproate was added with 9 cis RA and NCM that have been shown in our laboratory to promote neuronal differentiation. Rat cortical stem cells were differentiated with a daily treatment of either 0.5 mM of valproate, a 0.5× dilution of neuronal conditioned medium (NCM) or 1 nM of 9-cis retinoic acid for 7 days. Cells were also treated with valproate with NCM and/or 9cis RA. In the representative experiment described (FIG. 8), valproate, 9-cis RA and NCM when added alone increased the neuronal differentiation of rat stem cells compared to control (FIG. 8). When 9-cis RA and NCM were added together no additive effects was observed. Interestingly when added with 9-cis RA and NCM, valproate potentiates the neuronal differentiation to reach a maximum of 60% of neurons (FIG. 8). Other retinols may also be used.

Valproate increases the neuronal differentiation in human striatal stem cells. To verify that valproate can promote neurogenesis in human stem cells a non-transformed human stem cells line from striatum at passage 16 was expanded with growth factors for 4 weeks. Cells were then subcultured, dissociated as single cells and induced to differentiate by removal of growth factors. Human striatal stem cells were treated at the same time with valproate or BDNF for 9 days. In these conditions valproate increased the number of β tubulin III positive neurons compared to control and BDNF-treated cultures (FIG. 9A). As described previously for rat stem cells (FIGS. 1A–D) valproate was more efficient than BDNF in promoting neuronal differentiation and was not the result of an inhibition of cell proliferation as shown by the measure of the cell density (FIG. 9B).

The present invention is not to be limited in scope by the specific embodiments described herein. Indeed, various modifications of the invention in addition to those described herein will become apparent to those skilled in the art from the foregoing description and the accompanying figures. Such modifications are intended to fall within the scope of the appended claims. It is further to be understood that all numerical values, provided for description, are approximate.

All patents, patent applications, publications, and other materials cited herein are hereby incorporated herein reference in their entireties. In case of conflicting terminology, the present disclosure controls.

What is claimed is:

1. A method for preparing a population of mammalian neural cells enriched with neuronal cells in vitro, comprising the step of exposing a population of mammalian neural stem cells in growth factor-free medium to valproate in an amount and at a frequency of exposure sufficient to induce differentiation of said stem cells to express a neuronal cell marker.

2. The method of claim 1 wherein said mammalian neural stem cells are selected from the group consisting of adult, juvenile, and fetal neural stem cells.

3. The method of claim 1 wherein said population of mammalian neural cells comprises at least 90% neural stem cells.

4. The method of claim 1 wherein the amount of said valproate is within a range of between about 10 nM and about 10 mM.

5. The method of claim 1 wherein said frequency is daily.

6. The method of claim 1 wherein said frequency is every other day.

7. The method of claim 1 wherein the exposing step comprises adding said valproate to a culture medium and culturing said population in said medium.

8. The method of claim 1, wherein the duration of the exposure to valproate continues for a period of time within the range between about 2 and about 30 days.

9. The method of claim 8 wherein the period of time is about 6 days.

10. The method of claim 1, wherein the mammalian neural stem cells are human neural stem cells.

11. The method of claim 10, wherein the human neural stem cells are fetal human neural stem cells.

12. The method of claim 1, wherein the mammalian neural stem cells are rodent neural stem cells.

13. The method of claim 1, wherein the mammalian neural stem cells are derived from a primary culture comprising cortex, cerebellum or striatum neural stem cells.

14. The method of claim 1, wherein the cells differentiated into neurons comprise predominantly gamma aminobutyric acid-positive neurons.

15. The method of claim 4, wherein the amount of said valproate is about 0.5 mM.

16. The method of claim 1, further comprising exposing said mammalian neural stem cell population to 9-cis retinoic acid in an amount effective to further promote differentiation of said cells.

17. The method of claim 16, wherein the amount of 9-cis retinoic acid is in a range of about 1 nM to about 1 mM.

18. The method of claim 17, wherein the amount of 9-cis retinoic acid is about 1 nM.

19. The method of claim 13, further comprising exposing the mammalian neural stem cell population to neural conditioned medium in an amount effective to further promote differentiation of said cells.

20. The method of claim 3, wherein the proportion of said mammalian neural stem cells differentiated into neurons is at least about 30%.

21. The method of claim 20, wherein the proportion of mammalian neural stem cells differentiated into neurons is about 50%.

* * * * *